（12） United States Patent
Kohlweyer et al.

(10) Patent No.: US 12,319,038 B2
(45) Date of Patent: *Jun. 3, 2025

(54) CONSUMER PRODUCT PACKAGES

(71) Applicant: The Procter & Gamble Company, Cincinnati, OH (US)

(72) Inventors: Christian Kohlweyer, Bad Vilbel (DE); Paul Thomas Weisman, Cincinnati, OH (US); Michael Remus, Heidelberg (DE); Peter Kramkowski, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 359 days.

This patent is subject to a terminal disclaimer.

(21) Appl. No.: 17/539,527

(22) Filed: Dec. 1, 2021

(65) Prior Publication Data

US 2023/0166488 A1 Jun. 1, 2023

(51) Int. Cl.
*B32B 27/32* (2006.01)
*A61F 13/551* (2006.01)
(Continued)

(52) U.S. Cl.
CPC .......... *B32B 27/32* (2013.01); *A61F 13/5511* (2013.01); *B32B 1/00* (2013.01); *B32B 7/02* (2013.01); *B32B 27/08* (2013.01); *B32B 27/20* (2013.01); *B65D 65/42* (2013.01); *B65D 75/20* (2013.01); *B65D 75/56* (2013.01);
(Continued)

(58) Field of Classification Search
CPC .. B32B 27/32; B32B 1/00; B32B 7/02; B32B 27/08; B32B 27/20; B32B 2250/242; B32B 2270/00; B32B 2272/00; B32B 2439/40; B32B 2439/80; A61F 13/5511;
(Continued)

(56) References Cited

U.S. PATENT DOCUMENTS 4,522,775 A 6/1985 Briggs et al.
8,567,702 B2 10/2013 Kulesa et al.
(Continued)

FOREIGN PATENT DOCUMENTS

EP 3406666 A1 11/2018
EP 3858608 A1 8/2021
(Continued)

OTHER PUBLICATIONS

English machine translation for JP2020-511560 (Year: 2020).*
(Continued)

*Primary Examiner* — Michael C Miggins
(74) *Attorney, Agent, or Firm* — Christian M. Best

(57) ABSTRACT

A package containing polyolefin film having between about 10% and about 95%, by weight of the polyolefin film, of recycled polyolefin is described. The polyolefin film has an Average Hole Count between about 0.0 and about 10.0, according to the Gel Count Test Method. The polyolefin film has an Average Gel Count between about 0.0 and about 100.0, according to the Gel Count Test Method. The polyolefin film has an Average Relative Gel Height between about 0.0% and about 150.0%. The polyolefin film has a Total Spot Count between about 0.0 and about 100.0, according to the Gel Count Test Method.

22 Claims, 10 Drawing Sheets

(51) Int. Cl.
  *B32B 1/00*    (2024.01)
  *B32B 7/02*    (2019.01)
  *B32B 27/08*   (2006.01)
  *B32B 27/20*   (2006.01)
  *B65D 65/42*   (2006.01)
  *B65D 75/20*   (2006.01)
  *B65D 75/56*   (2006.01)
  *B65D 85/62*   (2006.01)

(52) U.S. Cl.
  CPC ........ *B65D 85/62* (2013.01); *B32B 2250/242* (2013.01); *B32B 2270/00* (2013.01); *B32B 2272/00* (2013.01); *B32B 2439/40* (2013.01); *B32B 2439/80* (2013.01)

(58) Field of Classification Search
  CPC ........ B65D 65/42; B65D 75/20; B65D 75/56; B65D 85/62
  See application file for complete search history.

(56) References Cited

U.S. PATENT DOCUMENTS

| | | |
|---|---|---|
| 8,820,666 B2 | 9/2014 | Kulesa et al. |
| 11,628,379 B2 | 4/2023 | Broyles et al. |
| 2004/0126524 A1 | 7/2004 | Longo et al. |
| 2012/0199675 A1 | 8/2012 | Kulesa et al. |
| 2019/0084206 A1 | 3/2019 | Deguchi et al. |
| 2019/0091077 A1 | 3/2019 | Cheng et al. |
| 2019/0126599 A1 | 5/2019 | Sargeant et al. |
| 2020/0263013 A1 | 8/2020 | De Palo et al. |
| 2021/0322894 A1 | 10/2021 | Broyles et al. |
| 2021/0370651 A1* | 12/2021 | Jones ............... B32B 7/12 |
| 2022/0227977 A1* | 7/2022 | Kleczek ............ B32B 27/32 |

FOREIGN PATENT DOCUMENTS

| | | |
|---|---|---|
| WO | 2016193186 A1 | 12/2016 |
| WO | 2020229932 A1 | 11/2020 |
| WO | 2021076351 A1 | 4/2021 |
| WO | 2021144136 A1 | 7/2021 |
| WO | 2021207342 A1 | 10/2021 |
| WO | 2022199857 A1 | 9/2022 |

OTHER PUBLICATIONS

English machine translation for JP2005-288729 (Year: 2005).*
Unpublished U.S. Appl. No. 18/461,806, filed Sep. 6, 2023, to Christian Kohlweyer et al.
All Office Actions; U.S. Appl. No. 18/461,806, filed Sep. 6, 2023.
All Office Actions; U.S. Appl. No. 17/539,538, filed Dec. 1, 2021.
Unpublished U.S. Appl. No. 17/539,538, filed Dec. 1, 2021, to Christian Kohlweyer et al.
PCT Search Report and Written Opinion for PCT/US2022/080548 dated Mar. 28, 2023, 15 pages.
All Office Actions; U.S. Appl. No. 19/042,053, filed Jan. 31, 2025.
Unpublished U.S. Appl. No. 19/042,053, filed Jan. 31, 2025, to Christian Kohlweyer et al.

* cited by examiner

CONSUMER PRODUCT PACKAGES

FIELD

The present disclosure is generally directed to consumer product packages having polyolefin films containing recycled polyolefin materials and having acceptable mechanical, visual, tactile, and/or chemical properties.

BACKGROUND

Consumer products are often packaged and sold at retail in soft packages formed of plastic polymer film. Plastic film is preferred as the primary package of many consumer products because plastic film may withstand the rigors of a packaging process, given a plastic film's ability to flex and stretch. Also, because plastic film can flex and stretch without tearing upon the application of force, opening features disposed in plastic packages tend to form clean openings while preserving the integrity of the rest of the package. In addition, plastic films can also protect consumer products from moisture and other contaminants during shipping and prior to use.

Consumer demand for products and packaging made at least partially from renewable and/or recycled resources has increased significantly over the past decade, and has become a driver of innovation for new and improved consumer products and packaging materials. In the context of plastic film-based packaging, one way to address this consumer demand is to replace at least a proportion of new petrol-based plastic material with plastic waste material, also known as recycled plastic material.

Adding recycled materials into the film manufacturing process, however, often negatively impacts the quality of the resulting flexible plastic film. Negative impacts on quality can manifest in a number of properties of the film, such as diminished mechanical properties (e.g., tensile strength or elongation at break), undesirable visual and tactile properties of the film material (e.g., dark spots, gels, etc.), contamination with foreign matter and/or trace chemicals, and/or reduced processability such as printing or sealing. Due to these problems, plastic film packages often comprise only relatively small amounts of recycled materials, and still exhibit resulting negative properties, such as visual defects and contamination with foreign matter and trace chemicals. As such, plastic films and packages formed from plastic films should be improved.

SUMMARY

Aspects of the present disclosure solve the problems discussed above by applying features of a high custody recycled material sourcing method to produce polyolefin films, and packages comprising such polyolefin films, comprising a significant amount (e.g., 10% to 95%, 25% to 95%, 30% to 95%, 40% to 95%, 50% to 95%) of recycled polyolefin and having acceptable mechanical, visual, tactile, and/or chemical properties. The high custody recycled material sourcing method includes storing post-consumer and/or post-industrial polyolefin material in controlled environments (e.g., humidity controlled environments, protective covers), removing impurities (e.g., metals, pallet labels, adhesive tapes), and applying traceability procedures (e.g., applying unique identifiers to discrete lots of recycled material). By following the high custody recycled material sourcing method, polyolefin films and packages comprising the same can incorporate a significant amount of recycled polyolefin content while not affecting the mechanical, visual, tactile, and/or chemical properties of the finished polyolefin film or package comprising such polyolefin film. Furthermore, the recycled films with high custody recycled material may be printable without visual defects, which are not consumer desired. In essence, the high custody sourcing method allows a significant amount of recycled polyolefin content to be incorporated while still producing a high quality film that is at parity, or almost at parity, to virgin polyolefin films. Such polyolefin films and packages comprising such polyolefin films with high recycled resin polyolefin content are consumer desirable while not negatively affecting the appearance or properties of the plastic film and packages comprising such films.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1:
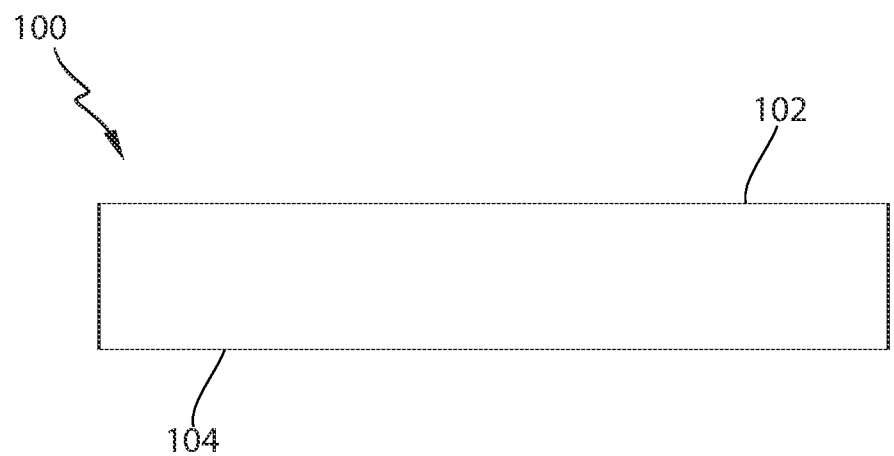
FIG. 1 is a schematic representation of a polyolefin film.

Various non-limiting forms of the present disclosure will now be described to provide an overall understanding of the principles of the structure, function, manufacture, and use of the consumer product packages disclosed herein. One or more examples of these non-limiting forms are illustrated in the accompanying drawings. Those of ordinary skill in the art will understand that the consumer product packages described herein and illustrated in the accompanying drawings are non-limiting example forms. The features illustrated or described in connection with one non-limiting form may be combined with the features of other non-limiting forms. Such modifications and variations are intended to be included within the scope of the present disclosure.

As used herein, "gel" and "gels" refer to any small defect that distorts a film product. Gels may originate from a variety of different sources, including oxidized polymeric materials, crosslinked polymeric materials, highly-entangled polymeric material, solid and/or unmelted resin, and contaminants (such as metal, dirt, wood, or other fragments).

As used herein, "virgin polyolefin material" refers to polyolefin material produced directly from the petrochemical or plant-based feedstock, such as natural gas, crude oil, or sugar cane, and which has never been used or processed before.

As used herein, "recycled polyolefin" and "recycled polyolefin material" refer to polyolefin material produced directly from materials other than petrochemical or plant-based feedstock, such as polyolefin material previously formed into films, containers, or other goods.

As used herein, "polyolefin resin" refers to polyolefin material in any form other than the form of a polyolefin film of the present disclosure, including pellets, molten form, precursor scrap film, and the like. "Polyolefin resin" may be in many different forms, including "recycled polyolefin resin," "post-industrial polyolefin resin," and "post-consumer polyolefin resin."

As used herein, "film" means a sheet structure having a length, width, and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

As used herein, "high density polyethylene" (HDPE) means a type of polyethylene defined by a density equal to or greater than 0.941 $g/cm^3$.

As used herein, "low density polyethylene" (LDPE) means a type of polyethylene defined by a density equal to or less than 0.925 $g/cm^3$.

As used herein, "medium density polyethylene" (MDPE) means a type of polyethylene defined by a density range of 0.926-0.940 $g/cm^3$.

As used herein, "linear low density polyethylene" (LLDPE) means a type of Low Density Polyethylene characterized by substantially linear polyethylene, with significant numbers of short branches, commonly made by copolymerization of ethylene with longer-chain olefins. Linear low-density polyethylene differs structurally from conventional low-density polyethylene (LDPE) because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces a LLDPE polymer that has a narrower molecular weight distribution than conventional LDPE and in combination with the linear structure, significantly different rheological properties.

As used herein, "consumer product" means diapers, pants, wet and dry wipes, tampons, adult incontinence products, paper towels, toilet tissue, facial tissue, items contained in film packages ordered from online or other sources, laundry soap or pods, dish soap or pods, air fresheners, laundry scent beads, sponges, cleaning compositions, stain removing products, cleaning products, dusting products, shaving devices, packages of blades for shaving, handles for shaving devices, shaving creams or gels, batteries, shampoo, lotions, deodorants, anti-perspirants, toothbrushes, toothbrush heads, toothbrush handles, tooth floss, mouthwash, denture adhesives, over the counter medicines, cough and cold products, antacids, fiber supplements, bar or liquid soap, beauty creams, make-up, lip balms, hair care products, skin care products, body sprays, and anti-aging creams and serums.

As used herein "Limit of Quantification" ("LOQ"), "Limit of Detection" ("LOD"), and "Reporting Limit" refer to the lowest quantity of a substance that can be distinguished from the absence of that substance.

One or more of the consumer products may be packaged in plastic, cardboard, paperboard, paper, metal, and/or other material containers (i.e., primary packaging), then those containers may be at least partially wrapped with the polyolefin films described herein (i.e., secondary packaging). An example is two plastic containers (i.e., primary packaging) of deodorant packaged together with a polyolefin film (i.e., secondary packaging) at least partially or fully wrapped around the two deodorant containers. Another example is a package of shaving blades in cardboard package (i.e., primary packaging) and then enclosed in a polyolefin film shipping package (i.e., secondary packaging).

Polyolefin Films

The present disclosure relates, in part, to polyolefin films comprising a significant amount of recycled polyolefin material and having acceptable mechanical, visual, tactile, and/or chemical properties, and packages comprising such polyolefin films. The polyolefin films of the present disclosure may comprise greater than 10%, greater than 20%, greater than 25%, greater than 30%, greater than 40%, greater than 50%, between about 10% and about 95%, between about 25% and about 95%, between about 30% and about 95%, between about 40% and about 95%, between about 45% and about 95%, or between about 50% and about 95%, by weight of the polyolefin film, of recycled polyolefin, specifically reciting every 1% increment within these ranges and all ranges formed therein or thereby.

The inclusion of recycled polyolefin materials in a polyolefin film, however, can negatively impact the quality of the resulting polyolefin film. Negative impacts on quality can manifest in a number of properties of the film, such as diminished mechanical properties (e.g., tensile strength or elongation at break), undesirable visual and tactile properties of the film material (e.g., dark spots, gels, etc.), contamination with foreign matter (e.g., wood, metal, trace chemicals), and/or reduced processability such as printing or sealing. The polyolefin films of the present disclosure may have acceptable mechanical, visual, tactile, and/or chemical properties.

One property associated with films comprising recycled material is the formation or presence of holes. A hole may comprise a visually discernible area of film where the absence film mass is apparent. Holes are not consumer or manufacturer desired in that products may not be sealed off from an external environment. Without wishing to be bound by theory, it is believed that contaminants brought in with recycled material and/or improper incorporation of recycled material into a newly-formed film may result numerous holes. The polyolefin films of the present disclosure, due to the high-custody recycled material sourcing method, may have an Average Hole Count between about 0.0 and about 10.0, or between about 0.0 and about 8.0, or between about 0.0 and about 5.0, or between about 0.0 and about 3.0, specifically reciting every 0.1 increment within these ranges and all ranges formed therein or thereby, according to the Gel Count Test Method disclosed herein. The polyolefin films of the present disclosure may be devoid of holes.

Another property associated with films comprising recycled material is the presence of gels. Without wishing to be bound by theory, it is believed that incorporation of increasing amounts of recycled material into a film may result in the formation of an increased number of gels in a finished film. Gels are not desired because they may distort printing of the films and/or appear to consumers as a defect. By employing the high-custody recycled polyolefin material sourcing methods, the polyolefin films of the present disclosure may have an Average Gel Count between about 0.0 and about 100.0, between about 0.0 and about 50.0, between about 0.0 and about 25.0, or between about 0.0 and about 5.0, specifically reciting every 0.1 increment within these ranges and all ranges formed therein or thereby, according to the Gel Count Test Method disclosed herein. The polyolefin films of the present disclosure may be devoid of gels.

It is also believed that the incorporation of increasing amounts of recycled material into a film may result in the formation of larger gels and/or gels that more prominently stand off from the surface of the film. These type of gels are not desired because they may distort printing of the films and/or appear to consumers as a defect. The polyolefin films of the present disclosure, because of the high-custody recycled polyolefin material sourcing method, may have an Average Gel Height of less than 150 mm, less than 90 mm, less than 60 mm, less than 45 mm, less than 30 mm, about 0.00 mm to about 150.00 mm, or of about 0.00 to about 90.00 mm, or of about 0.00 mm to about 60.00 mm, or of about 0.00 mm to about 45.00 mm, or of about 0.00 mm to about 30.00 mm, specifically reciting every 0.01 mm increment within these ranges and all ranges formed therein or thereby, according to the Gel Count Test Method disclosed herein. Alternatively, or in addition, the polyolefin films of the present disclosure may have an Average Relative Gel Height between about 0.0% and about 150.0%, between about 0.0% and about 125.0%, between about 0.0% and about 100.0%, between about 0.0% and about 75.0%, or between about 0.0% and about 50.0%, specifically reciting every 0.1% increment within these ranges and all ranges formed therein or thereby, according to the Gel Count Test Method disclosed herein.

Another property associated with films comprising recycled material is the presence of dark spots in the films or on the surface of the films. Dark spots are not desired because they may distort printing of the films or appear to consumers as a defect. Without wishing to be bound by theory, it is believed that the occurrence of dark spots may increase with an increasing amount of recycled material incorporated into a film due, at least in part, to increased contamination—especially carbon-containing contaminants—from the recycled material and/or recycled material receiving additional heat and processing steps. The polyolefin films of the present disclosure, employing the high-custody recycled polyolefin material sourcing method, may have a Total Spot Count between about 0.0 and about 100.0, between about 0.0 and about 50.0, between about 0.0 and about 25.0, or between about 0.0 and about 5.0, specifically reciting every 0.1 increment within these ranges and all ranges formed therein or thereby, according to the Gel Count Test Method disclosed herein. The polyolefin films of the present disclosure may be devoid of dark spots.

Additionally, or alternatively, dark spots may be measured on only one side of the film. The inventors have unexpectedly found the polyolefin films of the present disclosure may comprise consumer preferred low levels of dark spots on either and/or both sides of the polyolefin film. Without wishing to be bound by theory, the side comprising printed graphics may have a low level of dark spots and may result in consumer preferred printing quality. In addition, or alternatively, the side devoid of printed graphics may have a low level of dark spots for consumer preferred inside visual appearance. The side of the polyolefin film contacting the consumer product contained by the film may have a low level of dark spots alleviating the consumers perception of a visual contaminant on or in the polyolefin film potentially being in contact with the consumer product. Individual sided analysis of the polyolefin films of the present disclosure may be important where, for example, one side of a film is coated with an ink, rendering visualization of dark spots difficult.

The polyolefin films of the present disclosure, employing the high-custody recycled polyolefin material sourcing method, may have an Inner Surface Spot Count between about 0.0 and about 100.0, or between about 0.0 and 50.0, or between about 0.0 and about 25.0, or between about 0.0 and about 5.0 and/or an Outer Surface Spot Count of between about 0.0 and about 100.0, or between about 0.0 and 50.0, or between about 0.0 and about 25.0, or between about 0.0 and about 5.0, specifically reciting every 0.1 increment within these ranges and all ranges formed therein or thereby, according to the Gel Count Test Method disclosed herein.

Recycled polyolefin content of a polyolefin film may be determined using visual inspection. Manufacturers may advertise the use of recycled materials, and may also specify the percentage of recycled material. For example, visual inspection of a package comprising a polyolefin film may be used to identify logos or other indicia indicating the content and/or level of recycled polyolefin material. Additionally, or alternatively, visual inspection may include the use of a light box or microscopy to identify one or more of the common indicators of recycled content in polyolefin films, such as holes in the film, gels, and dark spots.

Due at least in part to the high-custody recycled polyolefin material sourcing method, the polyolefin films of the present disclosure may comprise significantly lower levels of certain trace chemicals as compared to traditional polyolefin films containing recycled materials. Without wishing to be bound by theory, it is believed that the inclusion of increasing amounts of recycled materials, which may have been exposed to environmental and/or other contaminants before being introduced into the polyolefin film manufacturing process, into a polyolefin film may result in increased levels of certain trace chemicals. Low levels of trace chemicals are consumer preferred.

The polyolefin films of the present disclosure may comprise less than 1,000 µg/kg, less 500 µg/kg, less than 150 µg/kg, less than 100 µg/kg, between about 0 µg/kg and about 1,000 µg/kg, between about 0 µg/kg and about 500 µg/kg, between about 0 µg/kg and about 150 µg/kg, or between about 0 µg/kg and about 100 µg/kg of isononylphenol (CAS RN 11066-49-2), specifically reciting every 1.0 µg/kg increment within these ranges and all ranges formed therein or thereby, according to the Trace Chemicals Test Method. The polyolefin films of the present disclosure may comprise between <LOQ and about 1,000 µg/kg, between <LOQ and about 500 µg/kg, between <LOQ and about 150 µg/kg, or between <LOQ and about 100 µg/kg of isononylphenol, specifically reciting every 1.0 µg/kg increment within these ranges and all ranges formed therein or thereby, according to the Trace Chemicals Test Method.

The polyolefin films of the present disclosure may comprise less than 75 ng/kg, less than 50 ng/kg, less than 25 ng/kg, between about 0 ng/kg and about 75 ng/kg, between about 0 ng/kg and about 50 ng/kg, or between about 0 ng/kg and about 25 ng/kg of PCB 77 (CAS RN 32598-13-3), specifically reciting every 1.0 ng/kg increment within these ranges and all ranges formed therein or thereby, according to the Trace Chemicals Test Method. The polyolefin films of the present disclosure may comprise between <LOQ and about 75 ng/kg, between <LOQ and about 50 ng/kg, or between <LOQ and about 25 ng/kg of PCB 77, specifically reciting every 1.0 ng/kg increment within these ranges and all ranges formed therein or thereby, according to the Trace Chemicals Test Method. PCB 77 is also known as 3,3',4,4'-Tetrachloro-1,1'-biphenyl, Polychlorinated biphenyl-77, and 3,3,4,4'-Tetrachlorobiphenyl.

The polyolefin films of the present disclosure may comprise less than 2,000 ng/kg, less than 1,000 ng/kg, less than 200 ng/kg, less than 100 ng/kg, between about 0 ng/kg and about 2,000 ng/kg, between about 0 ng/kg and about 1,000 ng/kg, between about 0 ng/kg and about 200 ng/kg, or between about 0 ng/kg and about 100 ng/kg of PCB 118 (CAS RN 31508-00-6), specifically reciting every 1.0 ng/kg increment within these ranges and all ranges formed therein or thereby, according to the Trace Chemicals Test Method. The polyolefin films of the present disclosure may comprise between <LOQ and about 2,000 ng/kg, between <LOQ and about 1,000 ng/kg, between <LOQ and about 200 ng/kg, or between <LOQ and about 100 ng/kg of PCB 118, specifically reciting every 1.0 ng/kg increment within these ranges and all ranges formed therein or thereby, according to the Trace Chemicals Test Method. PCB 118 is also known as 2,3',4,4',5-Pentachloro-1,1'-bipheny and 2,3',4,4',5-Pentachlorobiphenyl.

The polyolefin films of the present disclosure may comprise less than 45.00 ng/kg, less than 25.00 ng/kg, less than 5.00 ng/kg, less than 0.85 ng/kg, between about 0.00 ng/kg and about 45.00 ng/kg, between about 0.00 ng/kg and about 25.00 ng/kg, between about 0.00 ng/kg and about 5.00 ng/kg, or between about 0.00 ng/kg and about 0.85 ng/kg of OCDD (CAS RN 3268-87-9), specifically reciting every 0.01 ng/kg increment within these ranges and all ranges formed therein or thereby, according to the Trace Chemicals Test Method. The polyolefin films of the present disclosure may comprise between <LOQ and about 45.00 ng/kg, between <LOQ and about 25.00 ng/kg, <LOQ and about 5.00 ng/kg, or between <LOQ and about 0.85 ng/kg of OCDD, specifically reciting every 0.01 ng/kg increment within these ranges and all ranges formed therein or thereby, according to the Trace Chemicals Test Method. OCDD, a dioxin, is also known as 1,2,3,4,6,7,8,9-Octachlorodibenzo[b,e][1,4]dioxin, 1,2,3,4,6,7,8,9-Octachlorodibenzo-p-dioxin, and Octachlorodibenzo-p-dioxin.

The polyolefin films of the present disclosure may comprise less than 1.8 ng/kg, less than 1.2 ng/kg, less than 0.8 ng/kg, less than 0.2 ng/kg, between about 0.0 ng/kg and about 1.8 ng/kg, between about 0.0 ng/kg and about 1.2 ng/kg, between about 0.0 ng/kg and about 0.8 ng/kg, or between about 0.0 ng/kg and about 0.2 ng/kg of OCDF (CAS RN 39001-02-0), specifically reciting every 0.1 ng/kg increment within these ranges and all ranges formed therein or thereby, according to the Trace Chemicals Test Method. The polyolefin films of the present disclosure may comprise between <LOQ and about 1.8 ng/kg, between <LOQ and about 1.2 ng/kg, between <LOQ and about 0.8 ng/kg, or between <LOQ and about 0.2 ng/kg of OCDF, specifically reciting every 0.1 ng/kg increment within these ranges and all ranges formed therein or thereby, according to the Trace Chemicals Test Method. OCDF may be at a level below the limit of quantification, including 0, in the polyolefin films of the present disclosure. OCDF, a furan, is also known as 1,2,3,4,6,7,8,9-Octachlorodibenzofuran, Octachlorodibenzofuran, and Perchlorodibenzofuran.

The polyolefin films of the present disclosure may comprise less than 2,500 µg/kg, less than 1,000 µg/kg, less than 500 µg/kg, less than 100 µg/kg, less than 50 µg/kg, less than 5 µg/kg, between about 0 µg/kg and about 2,500 µg/kg, between about 0 µg/kg and about 1,000 µg/kg, between about 0 µg/kg and about 500 µg/kg, between about 0 µg/kg and about 100 µg/kg, between about 0 µg/kg and about 50 µg/kg, or between about 0 µg/kg and about 5 µg/kg of bisphenol A (CAS RN 80-05-7), specifically reciting every 1.0 µg/kg increment within these ranges and all ranges formed therein or thereby, according to the Trace Chemicals Test Method. The polyolefin films of the present disclosure may comprise between <LOQ and about 2,500 µg/kg, between <LOQ and about 1,000 µg/kg, between <LOQ and about 500 µg/kg, between <LOQ and about 100 µg/kg, between <LOQ and about 50 µg/kg, or between <LOQ and about 5 µg/kg of bisphenol A, specifically reciting every 1.0 µg/kg increment within these ranges and all ranges formed therein or thereby, according to the Trace Chemicals Test Method. Bisphenol A may be at a level below the limit of quantification, including 0, in the polyolefin films of the present disclosure. Bisphenol A is also known as BPA, 4,4'-(1-Methylethylidene)bis[phenol], 2,2-Bis(p-hydroxyphenyl)propane, 2,2-Bis(4-hydroxyphenyl)propane, and Bis(4-hydroxyphenyl)dimethylmethane.

The polyolefin films of the present disclosure may comprise less than 1,000 µg/kg, less than 500 µg/kg, less than 100 µg/kg, less than 50 µg/kg, between about 0 µg/kg and about 1,000 µg/kg, between about 0 µg/kg and about 500 µg/kg, between about 0 µg/kg and about 100 µg/kg, or between about 0 µg/kg and about 50 µg/kg of diisononyl phthalate (CAS RN 28553-12-0), specifically reciting every 1.0 µg/kg increment within these ranges and all ranges formed therein or thereby, according to the Trace Chemicals Test Method. The polyolefin films of the present disclosure may comprise between <LOQ and about 1,000 µg/kg, between <LOQ and about 500 µg/kg, between <LOQ and about 100 µg/kg, or between <LOQ and about 50 µg/kg of diisononyl phthalate, specifically reciting every 1.0 µg/kg increment within these ranges and all ranges formed therein or thereby, according to the Trace Chemicals Test Method. Diisononyl phthalate may be at a level below the limit of quantification, including 0, in the polyolefin films of the present disclosure. Diisononyl phthalate is also known as DINP, 1,2-Benzenedicarboxylic acid, 1,2-diisononyl ester, Phthalic acid, diisononyl ester, and 1,2-Benzenedicarboxylic acid, and diisononyl ester.

Recycled polyolefin may be categorized into several different classes. One class of recycled polyolefin may be "post-industrial polyolefin material" (also known as "PIPM", "post-industrial resin", or "PIR"). Post-industrial polyolefin material (PIPM) is waste and/or scrap generated in a manufacturing process that may be added back into the original manufacturing process. For example, the process of manufacturing a package comprising a polyolefin film may comprise a step of forming the polyolefin film, wherein waste and/or scrap polyolefin material is produced. When this waste and/or scrap polyolefin material is recycled into the polyolefin film forming step of the same manufacturing process, such waste and/or scrap polyolefin material may be termed PIPM. Additionally, waste and/or scrap polyolefin film portions of a finished package (such as a removed wicket panel) that is recycled into the polyolefin film forming step of the manufacturing process may also be termed PIPM, so long as the process forms a closed loop, being added back to the original manufacturing process. PIPM may be less prone to acquire contaminants because the PIPM material remains in a closed loop system, being recycled back into the original film manufacturing process. The polyolefin films of the present disclosure may comprise post-industrial polyolefin material as the recycled polyolefin. The polyolefin films of the present disclosure may comprise post-industrial polyolefin material as the recycled polyolefin, wherein the recycle polyolefin comprises polyethylenes (including LLDPE, LDPE, MDPE, and/or HDPE), polypropylene-ethylene interpolymer and copolymers having at least one olefinic constituent, and any mixtures thereof.

Another class of material may be "post-consumer polyolefin material" (also known as "PCPM", "post-consumer resin", or "PCR"). Post-consumer polyolefin material (PCPM) is polyolefin material that has been previously formed into an intermediate or final product form and is outside of the original manufacturing process as described above relative to the post-industrial polyolefin material. PCPM may be in the form of, for example, intermediate packaging material and/or finished packaging material. PCPM may be used or unused, meaning that the polyolefin material may, or may not, have been in contact with a consumer product, product, or packaged good, or otherwise utilized for its intended purpose. PCPM material may be diverted from landfills and/or collected from, for example, distribution centers, supermarkets, packaging material manufacturers, film and/or polyolefin resin manufacturers, food-producing plants, consumer product-producing plants, agricultural operations, and the like. PCPM may be utilized in the production of other commodities, including other polyolefin-containing commodities. PCPM may be prone to acquire significant amounts of contamination that may lead to reduced quality when recycled at significant levels into a new film. The polyolefin films of the present disclosure may comprise or consist of PCPM as the recycled polyolefin. The polyolefin films of the present disclosure may comprise or consist of PCPM as the recycled polyolefin, wherein the recycle polyolefin comprises polyethylenes (including LLDPE, LDPE, MDPE, and/or HDPE), polypropylene-ethylene interpolymer and copolymers having at least one olefinic constituent, and any mixtures thereof.

The polyolefin films of the present disclosure may, because of the high custody recycled resin sourcing method, comprise recycled polyolefin comprising less than 10,000 μg/kg, less 2,500 μg/kg, less than 750 μg/kg, less than 250 μg/kg, less than 50 μg/kg, between about 0 μg/kg and about 10,000 μg/kg, between about 0 μg/kg and about 5,000 μg/kg, between about 0 μg/kg and about 1,500 μg/kg, or between about 0 μg/kg and about 750 μg/kg of isononylphenol (CAS RN 11066-49-2), specifically reciting every 1.0 μg/kg increment within these ranges and all ranges formed therein or thereby, according to the Trace Chemicals Test Method. The polyolefin films of the present disclosure may comprise recycled polyolefin material comprising between <LOQ and about 10,000 μg/kg, between <LOQ and about 5,000 μg/kg, between <LOQ and about 1,500 μg/kg, or between <LOQ and about 750 μg/kg of isononylphenol, specifically reciting every 1.0 μg/kg increment within these ranges and all ranges formed therein or thereby, according to the Trace Chemicals Test Method.

The polyolefin films of the present disclosure may, because of the high custody recycled resin sourcing method, comprise recycled polyolefin material comprising less than 750 ng/kg, less than 500 ng/kg, less than 200 ng/kg, less than 50 ng/kg, between about 0 ng/kg and about 750 ng/kg, between about 0 ng/kg and about 500 ng/kg, or between about 0 ng/kg and about 200 ng/kg of PCB 77 (CAS RN 32598-13-3), specifically reciting every 1.0 ng/kg increment within these ranges and all ranges formed therein or thereby, according to the Trace Chemicals Test Method. The polyolefin films of the present disclosure may comprise recycled polyolefin material comprising between <LOQ and about 750 ng/kg, between <LOQ and about 500 ng/kg, or between <LOQ and about 200 ng/kg of PCB 77, specifically reciting every 1.0 ng/kg increment within these ranges and all ranges formed therein or thereby, according to the Trace Chemicals Test Method.

The polyolefin films of the present disclosure may, because of the high custody recycled resin sourcing method, comprise recycled polyolefin material less than 20,000 ng/kg, less than 10,000 ng/kg, less than 1,000 ng/kg, less than 150 ng/kg, between about 0 ng/kg and about 20,000 ng/kg, between about 0 ng/kg and about 10,000 ng/kg, between about 0 ng/kg and about 2,000 ng/kg, or between about 0 ng/kg and about 850 ng/kg of PCB 118 (CAS RN 31508-00-6), specifically reciting every 1.0 ng/kg increment within these ranges and all ranges formed therein or thereby, according to the Trace Chemicals Test Method. The polyolefin films of the present disclosure may comprise recycled polyolefin material comprising between <LOQ and about 20,000 ng/kg, between <LOQ and about 10,000 ng/kg, between <LOQ and about 2,000 ng/kg, or between <LOQ and about 850 ng/kg of PCB 118, specifically reciting every 1.0 ng/kg increment within these ranges and all ranges formed therein or thereby, according to the Trace Chemicals Test Method.

The polyolefin films of the present disclosure may, because of the high custody recycled resin sourcing method, comprise recycled polyolefin material comprising less than 450.0 ng/kg, less than 250.0 ng/kg, less than 50.0 ng/kg, less than 5.0 ng/kg, less than 0.5 ng/kg, between about 0.0 ng/kg and about 450.0 ng/kg, between about 0.0 ng/kg and about 250.0 ng/kg, between about 0.0 ng/kg and about 50.0 ng/kg, or between about 0.0 ng/kg and about 6.5 ng/kg of OCDD (CAS RN 3268-87-9), specifically reciting every 0.1 ng/kg increment within these ranges and all ranges formed therein or thereby, according to the Trace Chemicals Test Method. The polyolefin films of the present disclosure may comprise recycled polyolefin material between <LOQ and about 450.0 ng/kg, between <LOQ and about 250.0 ng/kg, <LOQ and about 50.0 ng/kg, or between <LOQ and about 6.5 ng/kg of OCDD, specifically reciting every 0.1 ng/kg increment within these ranges and all ranges formed therein or thereby, according to the Trace Chemicals Test Method.

The polyolefin films of the present disclosure may, because of the high custody recycled resin sourcing method, comprise recycled polyolefin material comprising less than 18.0 ng/kg, less than 10.0 ng/kg, less than 5.0 ng/kg, less than 0.4 ng/kg, between about 0.0 ng/kg and about 18.0 ng/kg, between about 0.0 ng/kg and about 12.0 ng/kg, between about 0.0 ng/kg and about 8.0 ng/kg, or between about 0.0 ng/kg and about 2.0 ng/kg of OCDF (CAS RN 39001-02-0), specifically reciting every 0.1 ng/kg increment within these ranges and all ranges formed therein or thereby, according to the Trace Chemicals Test Method. The polyolefin films of the present disclosure may comprise recycled polyolefin material between <LOQ and about 18.0 ng/kg, between <LOQ and about 12.0 ng/kg, between <LOQ and about 8.0 ng/kg, or between <LOQ and about 2.0 ng/kg of OCDF, specifically reciting every 0.1 ng/kg increment within these ranges and all ranges formed therein or thereby, according to the Trace Chemicals Test Method.

The polyolefin films of the present disclosure may, because of the high custody recycled resin sourcing method, comprise recycled polyolefin material comprising less than 25,000 µg/kg, less than 10,000 µg/kg, less than 5,000 µg/kg, less than 1,000 µg/kg, less than 500 µg/kg, less than 50 µg/kg, less than 20 µg/kg, between about 0 µg/kg and about 25,000 µg/kg, between about 0 µg/kg and about 10,000 µg/kg, between about 0 µg/kg and about 5,000 µg/kg, between about 0 µg/kg and about 1,000 µg/kg, between about 0 µg/kg and about 500 µg/kg, or between about 0 µg/kg and about 50 µg/kg of bisphenol A (CAS RN 80-05-7), specifically reciting every 1.0 µg/kg increment within these ranges and all ranges formed therein or thereby, according to the Trace Chemicals Test Method. The polyolefin films of the present disclosure may comprise recycled polyolefin material comprising between <LOQ and about 25,000 µg/kg, between <LOQ and about 10,000 µg/kg, between <LOQ and about 5,000 µg/kg, between <LOQ and about 1,000 µg/kg, between <LOQ and about 500 µg/kg, or between <LOQ and about 50 µg/kg of bisphenol A, specifically reciting every 1.0 µg/kg increment within these ranges and all ranges formed therein or thereby, according to the Trace Chemicals Test Method.

The polyolefin films of the present disclosure may, because of the high custody recycled resin sourcing method, comprise recycled polyolefin material comprising less than 10,000 µg/kg, less than 5,000 µg/kg, less than 1,000 µg/kg, less than 500 µg/kg, between about 0 µg/kg and about 10,000 µg/kg, between about 0 µg/kg and about 5,000 µg/kg, between about 0 µg/kg and about 1,000 µg/kg, or between about 0 µg/kg and about 500 µg/kg of diisononyl phthalate (CAS RN 28553-12-0), specifically reciting every 1.0 µg/kg increment within these ranges and all ranges formed therein or thereby, according to the Trace Chemicals Test Method. The polyolefin films of the present disclosure may comprise recycled polyolefin material comprising between <LOQ and about 10,000 µg/kg, between <LOQ and about 5,000 µg/kg, between <LOQ and about 1,000 µg/kg, or between <LOQ and about 500 µg/kg of diisononyl phthalate, specifically reciting every 1.0 µg/kg increment within these ranges and all ranges formed therein or thereby, according to the Trace Chemicals Test Method.

Referring to FIG. 1, the polyolefin film 100 may comprise a first surface 102 and a second surface 104. For purposes of balancing economy of material usage and maximization of tensile strength of the film, the polyolefin film 100 may have a thickness (caliper) of from about 20 µm to about 100 µm, from about 25 µm to about 98 µm, or from about 28 µm to about 95 µm, specifically reciting every 1.0 µm increment within these ranges and all ranges formed therein or thereby. The polyolefin film 100 of the present disclosure may be a flexible film. As used herein, the term "flexible" refers to a relatively thin, easily deformable material, as opposed to a "rigid" material that exhibits resistance to deformation. The polyolefin film 100 of the present disclosure may not be a rigid film.

Figure 2:
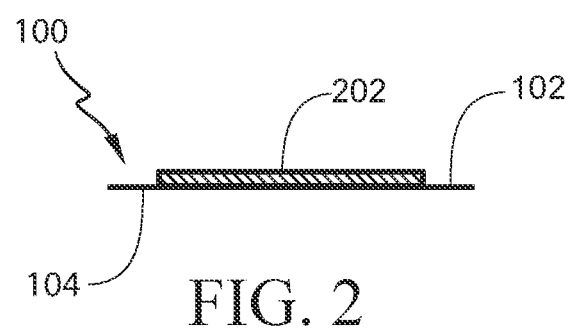
FIG. 2 is a schematic representation of a polyolefin film comprising printed graphics disposed on a first surface of the polyolefin film.
Figure 3:
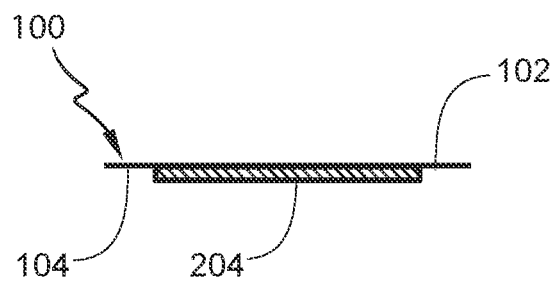
FIG. 3 is a schematic representation of a polyolefin film comprising printed graphics disposed on a second surface of the polyolefin film.

The first surface 102 of the polyolefin film 100 may comprise a printed graphic 202, as shown in FIG. 2, or may be free of a printed graphic. The second surface 104 may comprise a printed graphic 204, as shown in FIG. 3, or may be free of a printed graphic. A "graphic" may include the depiction of a design or designs, any recognizable indicia such as a number, a letter, a word, a brand name, an icon, a logo, a character, any shape and/or symbol (for example hearts, clouds, animals, etc.), as well as a full flood of pigment across the surface, or a portion of the surface, of the polyolefin film. In a form, the first surface 102 may comprise a printed graphic and the second surface 104 may be devoid of a printed graphic. In another form, the first surface 102 may be devoid of a printed graphic and the second surface 104 may comprise a printed graphic. The printed graphic may be formed by ink or any other pigmented medium known in the art.

The polyolefin films of the present disclosure may be formed from a single layer of polyolefin material (including recycled polyolefin material)—a monolayer film, —or may be formed from a laminate of more than one layer of polyolefin material—a multilayer film. A multilayer film may have, for example, a first skin layer formed of a first polymer and a second skin layer formed of a second polymer. Either of the skin layers may contain recycled polyolefin material. The first polymer and the second polymer may be the same, or may be different.

A multilayer film may have layers of polyolefin compositions particularly chosen for the characteristics they impart to the film. For example, one or two skin layers may be formed of compositions chosen for, e.g., surface gloss; printability; smooth feel; pliability; low noise generation (upon being handled and manipulated, as by a consumer); relatively lower melt temperature and fusibility/weldability; low oxygen permeability; low moisture permeability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics.

Each of the layers may include a base polyolefin. Base polyolefins may include polyethylenes (including LLDPE, LDPE, MDPE, and/or HDPE), polypropylenes, polybutadienes, polypropylene-ethylene interpolymer and copolymers having at least one olefinic constituent, and any mixtures thereof.

Figure 4:
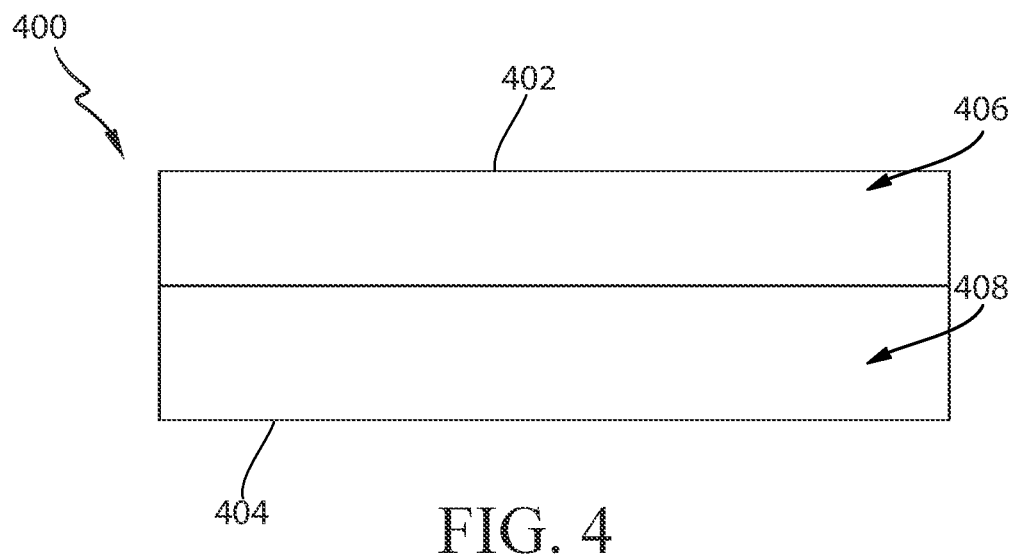
FIG. 4 is a schematic representation of a multilayer polyolefin film comprising two layers.
Figure 5:
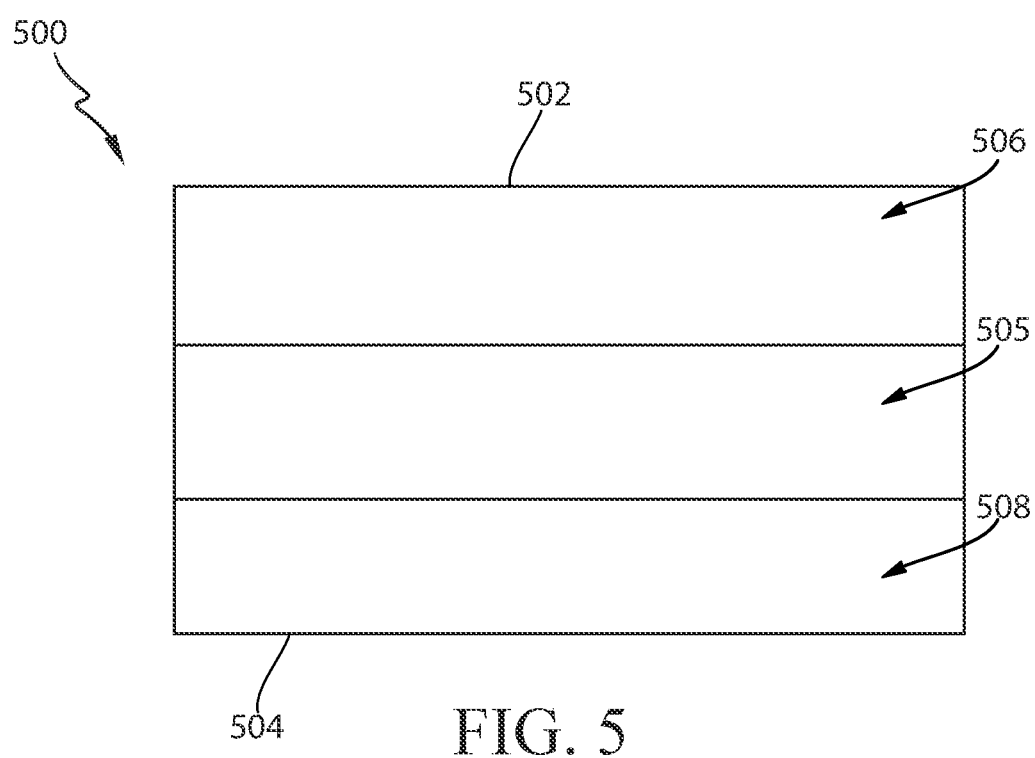
FIG. 5 is a schematic representation of a multilayer polyolefin film comprising three layers.

Referring to FIGS. 4 and 5, the polyolefin films 400, 500 of the present disclosure may be formed from two or more layers of polyolefin material. As shown in FIG. 4, the polyolefin film 400 comprises a first film layer 406 and a second film layer 408. The first film layer 406 may form the first surface 402 of the polyolefin film 400. The second film layer 408 may form the second surface 404 of the polyolefin film 400. As shown in FIG. 5, an intermediate film layer 505 may be disposed between a first film layer 506 and a second layer 508. The first film layer 506 may form the first surface 502, and the second film layer 508 may form the second surface 504.

The different layers of the multilayer films of the present disclosure may differ in thickness (caliper). Referring to FIG. 5, the intermediate film layer 505 may have a greater thickness than the first film layer 506 and/or the second film layer 508. The thickness of the first film layer 506 and/or the second film layer 508 may be approximately one-half the thickness of the intermediate film layer 505. In a form, the thicknesses of the different layers of the multilayer films may be in a ratio of 1:2:1 (first film layer:intermediate film layer:second film layer). In another form, the thicknesses of the different layers of the multilayer films may be in a ratio of 0.5:2:0.5 (first film layer:intermediate film layer:second film layer). In yet another form, the thicknesses of the different layers of the multilayer films may be in a ratio of 0.5:2:1 (first film layer:intermediate film layer:second film layer).

The individual layers of the multilayer films of the present disclosure may comprise the same polyolefin material, or may comprise different polyolefin materials. Referring again to FIG. 4, the first film layer 406 may comprise recycled polyolefin material, whereas the second film layer 408 may be devoid of (free of) recycled polyolefin material. In another form, the first film layer 406 may be devoid of recycled polyolefin material, whereas the second film layer 408 may comprise recycled polyolefin material. In yet another form, the first film layer 406 and the second film layer 408 may comprise recycled polyolefin material at different levels or the same levels. Referring to FIG. 5, the intermediate film layer 505 may comprise recycled polyolefin material, whereas the first film layer 506 and the second film layer 508 may be devoid of recycled polyolefin material. In another form, the intermediate film layer 505 may be devoid of recycled polyolefin material, whereas the first film layer 506 and/or the second film layer 508 may comprise recycled polyolefin material. In yet another form, the first film layer 506, the second film layer 508, and the intermediate film layer 505 may each comprise the same, or different, amounts of recycled polyolefin material. As discussed herein, the first film layer 506 and the second film layer 508, i.e., the outer-most layers of the polyolefin film, may be formed of compositions chosen for their functional characteristics, such as gloss, printability, low permeability, etc. The outer-most layers, or at least one of the outer-most layers of the polyolefin film may also be formed of only virgin polyolefin material in order to provide a barrier between a layer of the film comprising recycled polyolefin material and a consumer product.

A multilayer film as contemplated herein may comprise one or more tie layers disposed between other layers. A tie layer may be necessary when the polymers of adjoining layers would not otherwise be miscible or compatible so as to bond to each other during extrusion. For example, a tie layer between a polyethylene skin layer and an intermediate layer having a large polylactic acid content may be deemed desirable. Thus, for example, in a multilayer film having three main layers—two skin layers and an intermediate layer disposed between them, tie layers may be disposed between the intermediate layer and each of the skin layers. A tie layer may include one or more functionalized polyolefins. In some example, a tie layer may include from 5%, 10%, 20%, 30%, 40% or 45% to 55%, 60%, 70%, 80%, 90%, or 100%, by weight of the tie layer, of the one or more functionalized polyolefins. A tie layer may consist essentially of the one or more functionalized polyolefins.

The tie layer may comprise a functionalized polyolefin that possesses a polar component provided by one or more functional groups that is compatible with the materials of the intermediate layer(s) and a non-polar component provided by an olefin that is compatible with one or more polyolefins of the adjacent skin layer. The polar component may, for example, be provided by one or more functional groups and the non-polar component may be provided by an olefin. The olefin component may generally be formed from any linear or branched α-olefin monomer, oligomer, or polymer (including copolymers) derived from an olefin monomer. The α-olefin monomer typically has from 2 to 14 carbon atoms and preferably from 2 to 6 carbon atoms. Examples of suitable monomers include, but not limited to, ethylene, propylene, butene, pentene, hexene, 2-methyl-1-propene, 3-methyl-1-pentene, 4-methyl-1-pentene, and 5-methyl-1-hexene. Examples of polyolefins include both homopolymers and copolymers, i.e., polyethylene, ethylene copolymers such as EPDM, polypropylene, propylene copolymers, and polymethylpentene polymers.

An olefin copolymer can include a minor amount of non-olefinic monomers, such as styrene, vinyl acetate, diene, or acrylic and non-acrylic monomer. Functional groups may be incorporated into the polymer backbone using a variety of known techniques. For example, a monomer containing the functional group may be grafted onto a polyolefin backbone to form a graft copolymer. Such grafting techniques are well known in the art and described, for instance, in U.S. Pat. No. 5,179,164. In other embodiments, the monomer containing the functional groups may be copolymerized with an olefin monomer to form a block or random copolymer. Regardless of the manner in which it is incorporated, the functional group of the compatibilizer may be any group that provides a polar segment to the molecule, such as a carboxyl group, acid anhydride group, acid amide group, imide group, carboxylate group, epoxy group, amino group, isocyanate group, group having oxazoline ring, hydroxyl group, and so forth. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation POLYBOND and Eastman Chemical Company under the designation Eastman G SERIES, and AMPLIFY™ GR Functional Polymers (maleic anhydride grafted polyolefins). Other examples include LOTADER AX8900 (polyethylene—methyl acrylate—glycidyl methacrylate terpolymer) and LOTADER TX 8030 (polyethylene—acrylic ester-maleic anhydride terpolymer) available from Arkema, Columbes, France.

In some aspects, the tie layer can be a resin composition as disclosed in U.S. Pat. No. 8,114,522. This resin composition includes a modified PO resin and a terpene resin. Alternatively, it includes a polylactic acid resin, a modified polyolefin resin, and a hydrogenated petroleum resin. These compositions are suitable for use as a tie layer between the outer layer and the core layer.

In some examples, an outer layer and tie layer may be essentially combined as an outer layer by incorporating a functionalized polyolefin into one or both of the outer layers. In these instances, the multi-layer film may comprise 3 or 4 layers. In the case of a 3 layer film, the film may comprise a first outer layer comprising a polyolefin and/or a functionalized polyolefin, one or more core layers, and a second outer layer comprising a polyolefin and/or a functionalized polyolefin). In the case of a 4 layer film, the film may comprise a first outer layer comprising a polyolefin and/or a functionalized polyolefin, one or more core layers, a tie layer, and a second outer layer comprising a polyolefin.

Multilayer polyolefin films of the present disclosure may be formed by any process known in the art, including co-extrusion and lamination. Where multilayer polyolefin films are formed by lamination, an adhesive may be applied, for example by printing, to one or multiple surfaces of film layers that are subsequently brought into contact with each other and joined.

Any of the layers of the multilayer film may comprise small amounts of one or more additives. Typically, the additives may comprise less than about 15%, 10%, 5%, 4%, 3%, 2%, 1%, 0.5%, 0.1%, 0.01%, or between about 0.01% and about 15%, between about 0.1% and about 10%, or between about 0.5% and about 10% by weight of the layer of the additive. Some non-limiting examples of classes of additives contemplated include perfumes, dyes, pigments, nanoparticles, antistatic agents, fillers, and combinations thereof. The layers disclosed herein can contain a single additive or a mixture of additives. For example, both a perfume and a colorant (e.g., pigment and/or dye) can be present.

A pigment or dye can be inorganic, organic, or a combination thereof. Specific examples of pigments and dyes contemplated include pigment Yellow (C.I. 14), pigment Red (C.I. 48:3), pigment Blue (C.I. 15:4), pigment Black (C.I. 7), and combinations thereof. Specific contemplated dyes include water soluble ink colorants like direct dyes, acid dyes, base dyes, and various solvent soluble dyes. Examples include, but are not limited to, FD&C Blue 1 (C.I. 42090:2), D&C Red 6 (C.I. 15850), D&C Red 7 (C.I. 15850:1), D&C Red 9 (C.I. 15585:1), D&C Red 21 (C.I. 45380:2), D&C Red 22 (C.I. 45380:3), D&C Red 27 (C.I. 45410:1), D&C Red 28 (C.I. 45410:2), D&C Red 30 (C.I. 73360), D&C Red 33 (C.I. 17200), D&C Red 34 (C.I. 15880:1), and FD&C Yellow 5 (C.I. 19140:1), FD&C Yellow 6 (C.I. 15985:1), FD&C Yellow 10 (C.I. 47005:1), D&C Orange 5 (C.I. 45370:2), and combinations thereof.

Contemplated fillers include, but are not limited to, inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins can comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g., sodium benzoate and lithium benzoate), as well as kaolin, talc, and zinc glycerolate. Dibenzlidene sorbitol (DBS) is an example of a clarifying agent that can be used. Other nucleating agents that can be used are organocarboxylic acid salts, sodium phosphate and metal salts (e.g., aluminum dibenzoate). In one aspect, the nucleating or clarifying agents can be added in the range from 20 parts per million (20 ppm) to 20,000 ppm, or from 200 ppm to 2000 ppm, or from 1000 ppm to 1500 ppm. The addition of the nucleating agent can be used to improve the tensile and impact properties of the finished composition.

Additional contemplated additives include slip agents for purposes of reducing the coefficient of friction on one or both of the two outside surfaces of the film, or as antiblocking agents. Suitable additives for this purpose may include but are not limited to fatty amides, for example, erucamide.

Additives may also include antioxidants such as BHT, and IRGANOX products, for example, IRGANOX 1076 and IRGANOX 1010. IRGANOX products are available from BASF Corporation, Florham Park, NJ, USA. Antioxidants may help reduce degradation of the film through oxidation, particularly during processing.

Contemplated surfactants include anionic surfactants, amphoteric surfactants, or a combination of anionic and amphoteric surfactants, and combinations thereof, such as surfactants disclosed, for example, in U.S. Pat. Nos. 3,929,678 and 4,259,217, and in EP 414549, WO93/08876, and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, bentonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides (Fe2O3, Fe3O4) and mixtures thereof. Nanoparticles can increase strength, thermal stability, and/or abrasion resistance of the compositions disclosed herein, and can give the compositions electric properties.

Contemplated anti-static agents include fabric softeners that are known to provide antistatic benefits. These can include those fabric softeners having a fatty acyl group that has an iodine value of greater than 20, such as N,N-di (tallowoyl-oxy-ethyl)-N,N-dimethyl ammonium methylsulfate.

In particular aspects, the filler can comprise renewable fillers. These can include, but are not limited to, lipids (e.g., hydrogenated soybean oil, hydrogenated castor oil), cellulosics (e.g., cotton, wood, hemp, paperboard), lignin, bamboo, straw, grass, kenaf, cellulosic fiber, chitin, chitosan, flax, keratin, algae fillers, natural rubber, nanocrystalline starch, nanocrystalline cellulose, collagen, whey, gluten, and combinations thereof.

Particular combinations of film layers, film layer compositions and pigment additives for maximizing package film opacity while providing a film that effectively balances weldability, tensile strength and cost effectiveness are described in PCT Application No. CN2016/088098, the disclosure of which is incorporated herein by reference.

Packages

The polyolefin films of the present disclosure may form at least a portion of a package. The package may comprise the polyolefin films of the present disclosure, may be formed from the polyolefin films of the present disclosure, or may be formed entirely from the polyolefin films of the present disclosure.

Figure 6:
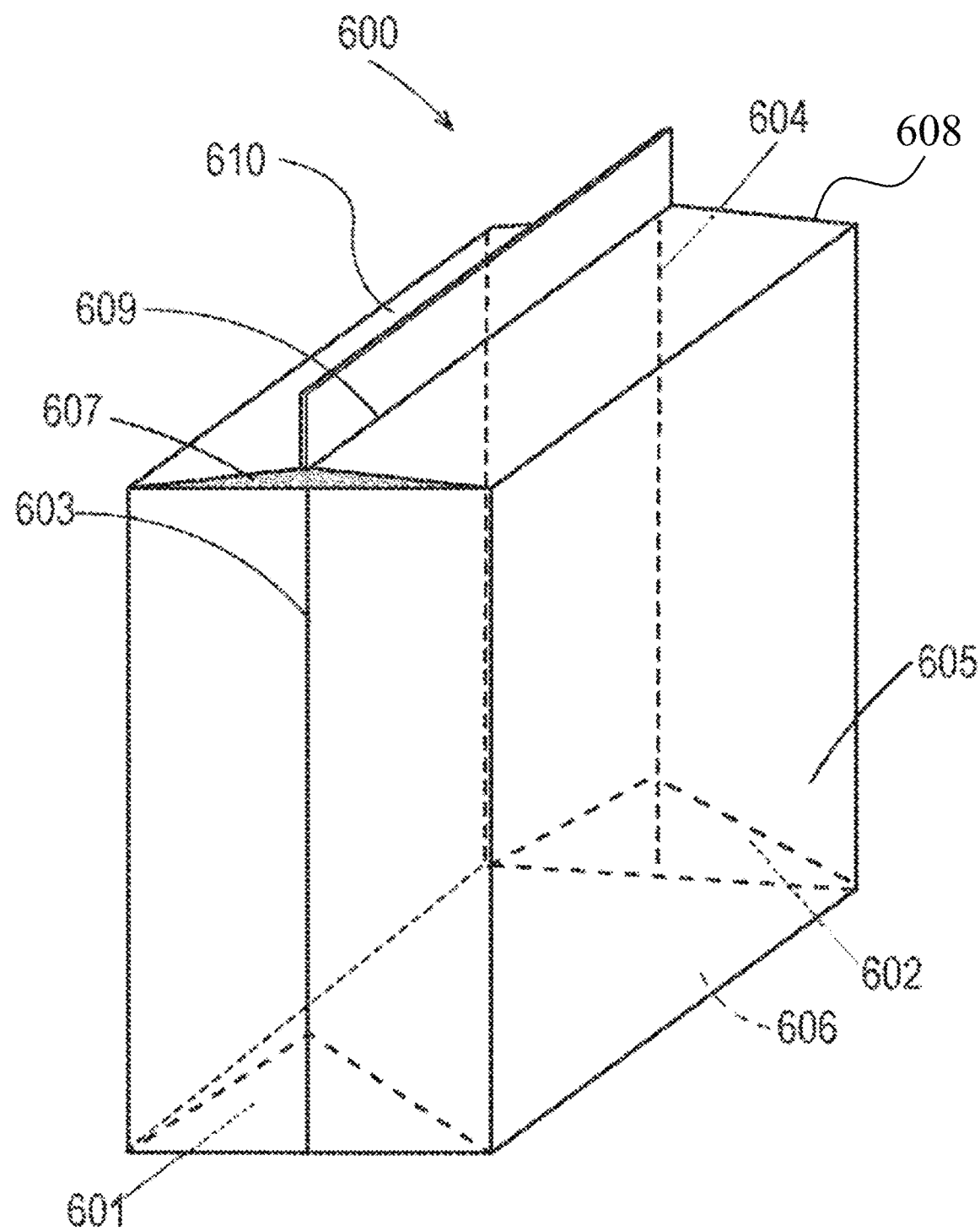
FIG. 6 is a schematic representation of a package formed at least partially from a polyolefin film.

The packages may take any shape and size and be suitable for a consumer product to be contained therein or partially therein. For example, the package may comprise a plurality of panels which define an interior compartment and at least partially enclose one or more than one consumer product. The packages of the present disclosure may be formed from a single sheet of polyolefin film of the present disclosure suitably folded to form a bag structure, as shown in FIG. 6. A package 600 may be formed from a single sheet of polyolefin film that is suitably folded to form bag gussets 601, 602 and then joined along portions by bonding to form two side seams 603, 604 on opposite sides, to form a bag structure with no seam on a first package surface 605, and open at the other end (e.g., a gusseted bag structure). Thereafter, the bag structure may be filled by inserting the consumer product through the open end. The open end opposite first package surface 606 may then be closed by suitably folding to form closing gussets 607, 608, bringing the polyolefin film edges together, and bonding them together to form end seam 609 and second package surface 610.

Figure 7:
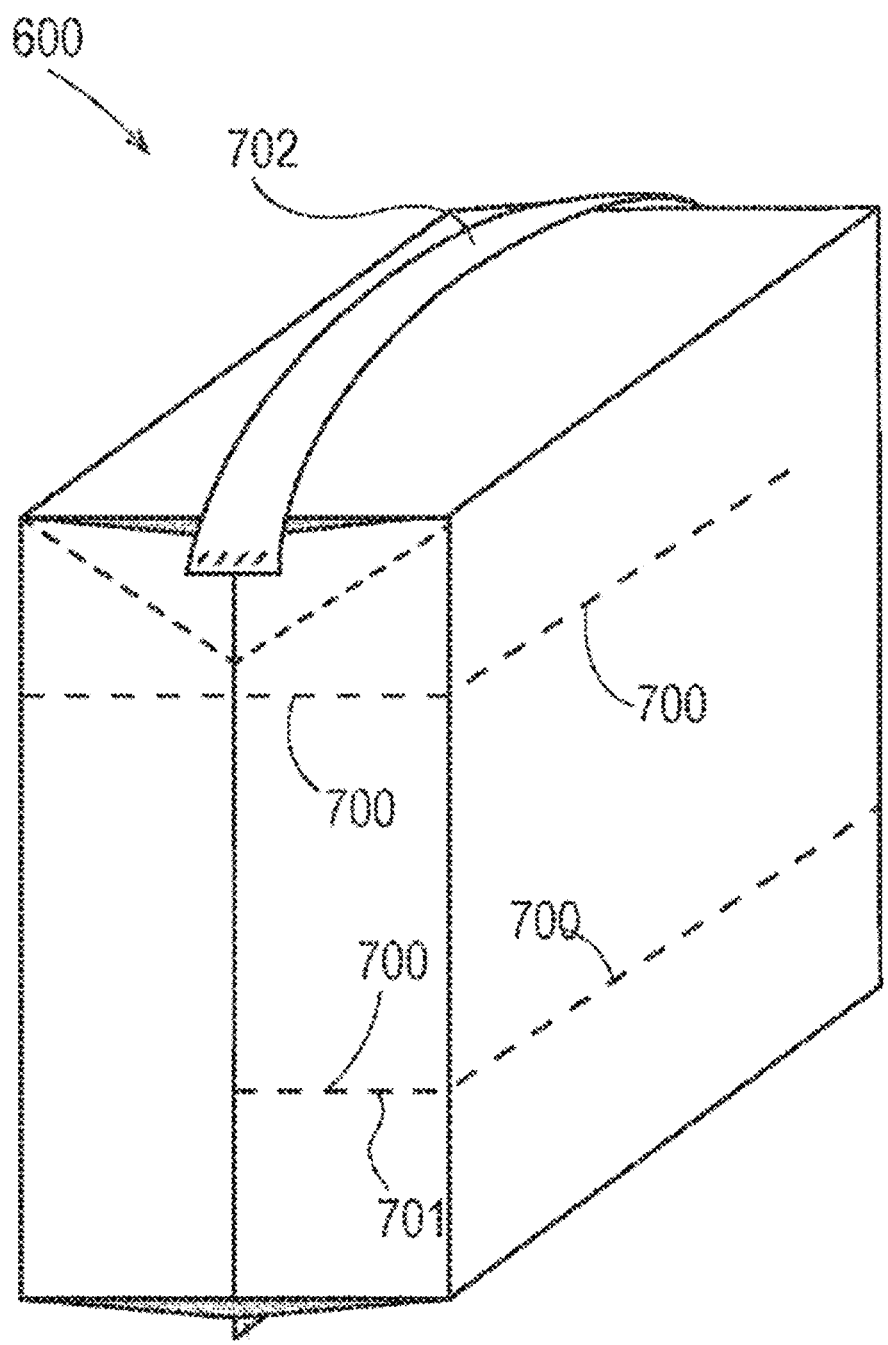
FIG. 7 is a schematic representation of a package formed at least partially from a polyolefin film having a handle and an opening feature.

Referring to FIG. 7, the packages 600 may include an opening feature 700 along a top or bottom edge portion of the package for opening the package 600. The opening feature 700 may, for example, be a perforation or line of perforations 701. The opening feature 700 may be reclosable. The reclosable features may include a lid, tape tab fastener, hook and loop fastener, snap, button, or latch, for example. The package 600 may also comprise a handle 702 for ease of carrying.

Figure 8:
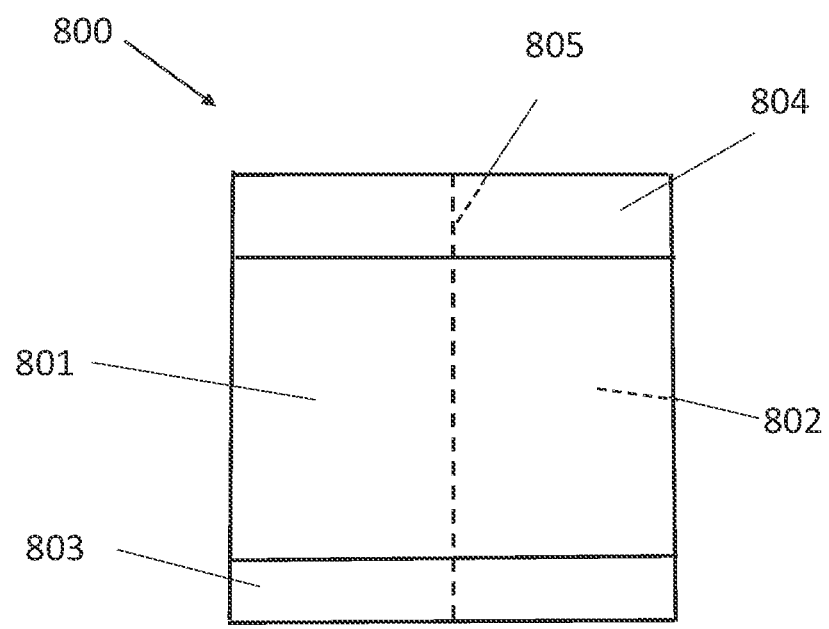
FIG. 8 is a schematic representation showing a package constructed with a flow wrap process.

Other package shapes are contemplated, including flow wrap or horizontal form fill-and-seal wrap comprising polyolefin films of the present disclosure. Referring to FIG. 8, a flow wrap package 800 may comprise a first surface 801 and an opposing second surface 802. Rounded edges may be provided as a transition between the first surface 801 and the second surface 802. One or more fold lines may be provided between the first surface 801 and the second surface 802. The flow wrap package 800 may further comprise end seals 803 and 804, and a hoop seam 805 which may be disposed on the second surface 802. Flow wrap packages may be useful, particularly where a low number of products are included within a package.

Bonds forming any or all of the package seals, such as seams, may be created by welding. (Herein, "weld" refers to a union between separate portions of polyolefin film, effected by application of direct or indirect (e.g., ultrasonic) heating energy and pressure that causes separate portions of the film to at least partially melt and fuse together to some extent, forming a bonded area, joint, or seam which cannot be separated without substantial destruction to the remainder of one or both joined portions.) If package-forming machinery forms welds in the polyolefin film that join the film stock to itself by applying heating energy that causes the film to fuse to itself, it may be desirable that the film stock be multilayer film, and that the layer(s) to be brought into contact and fused be formed of polymer(s) that have lower melting temperature(s) than those of the polymer(s) used to form the other layer(s). This enables heating energy to be applied to a degree sufficient to heat the layer(s) in contact and cause them to fuse, but not sufficient to cause undesired melting and deformation of the other layer(s), which could cause the package to be misshapen and/or displace and/or distort printing on the film stock.

Figure 9:
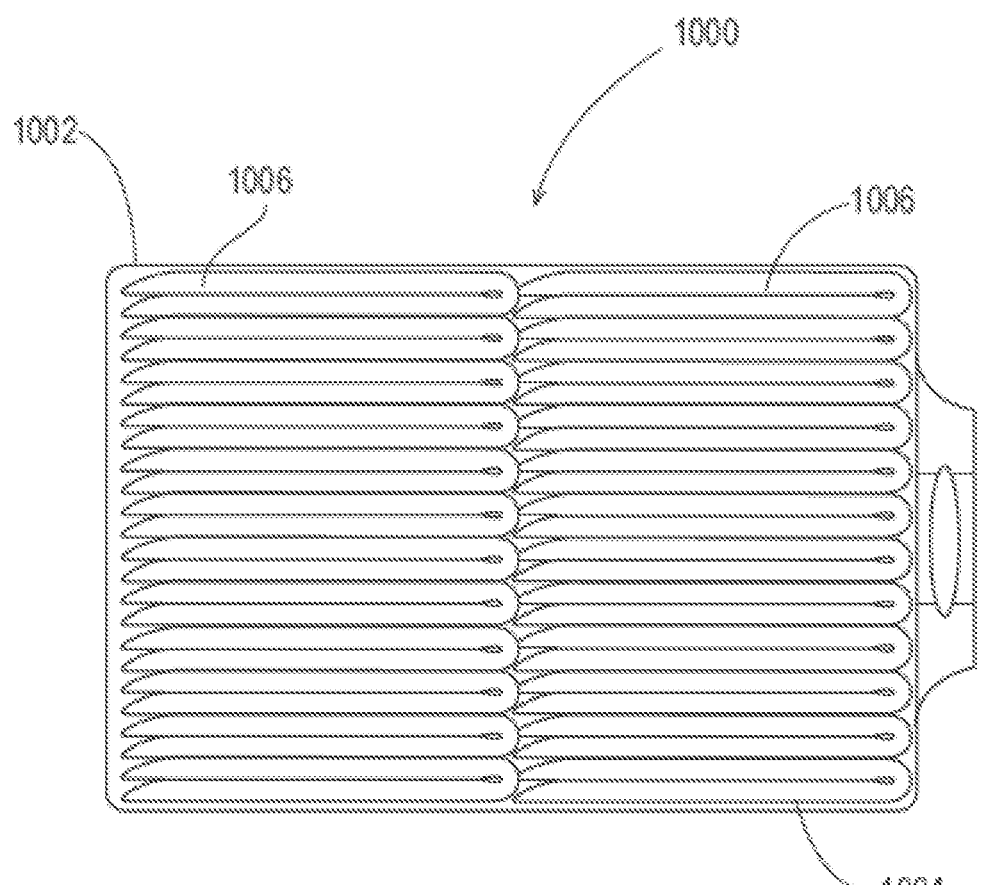
FIG. 9 is a cross-sectional view of the package showing consumer products disposed therein.

The packages of the present disclosure may comprise a polyolefin film of the present disclosure and a consumer product. As shown in FIG. 9, the packages 1000 may define an interior compartment 1002 such that the polyolefin film may at least partially enclose one or more than one consumer product 1004. The polyolefin film may be disposed around and fully enclose the consumer product. The consumer product may be disposed within the polyolefin film. In a form, the packages of the present disclosure consist of the polyolefin films of the present disclosure.

Referring again to FIG. 1, the polyolefin film 100 of the package may be oriented such that the first surface 102 faces away from the consumer product, and the second surface 104 faces toward the consumer product. In such a form, the first surface may be considered the outer surface of the polyolefin film and/or package, and the second surface may be considered the inner surface of the polyolefin film and/or package. In another form, the first surface 102 may face toward the consumer product, and the second surface 104 may face away from the consumer product. In such a form, the second surface may be considered the outer surface of the polyolefin film and/or package, and the first surface may be considered the inner surface of the polyolefin film and/or package. The specific orientation of the polyolefin film may be beneficial, for example, when only one surface of the polyolefin film comprises printed graphics. In certain package configurations, it may be desirable to have printed graphics only on the outer surface of the polyolefin film facing away from the consumer product. This configuration may be beneficial because it may reduce or prevent ink, or other materials used in printing graphics, from rubbing off on the consumer product in the package.

The specific orientation of the polyolefin films relative to the consumer product may be relevant to multilayer polyolefin films as well. Referring to FIGS. 4 and 5, the first surfaces 402/502 may be oriented facing away or toward the consumer product. The second surfaces 404/504 may be oriented facing away or toward the consumer product. As discussed, multilayer polyolefin films may exhibit sidedness because the different layers of the multilayer polyolefin films may provide different characteristics or functionalities. It may therefore be beneficial that the first and/or second surface face away from the consumer product. For example, the first layer of a multilayer polyolefin film may form the first surface of the film, and the first layer may have been selected because it readily receives and retains printed graphics. As such, it may be desirable that the first surface face away from the consumer product and toward the consumer. In another example, it may be desirable that the second polyolefin layer 408/508 forms the second surface 404/504 that faces the consumer product, and that the second polyolefin layer 408/508 is free of recycled polyolefin material. It may be desirable that the consumer product only come in contact with a portion of the polyolefin film that comprises virgin polyolefin material, or is otherwise free of recycled polyolefin material.

Packages of the present disclosure may comprise a polyolefin film as described herein, wherein the first surface of the polyolefin film forms an outer surface of the package facing away from the consumer product, and wherein the second surface of the polyolefin film forms an inner surface facing toward the consumer product. At least a portion of the second surface of the polyolefin film may be in contact with the consumer product or may be in contact with primary packaging of the consumer product. The polyolefin film may comprise more than one polyolefin layer, and the layer forming the second surface may be devoid of recycled polyolefin material.

Packages of the present disclosure may comprise a polyolefin film as described herein, wherein the second surface of the polyolefin film forms an outer surface of the package facing away from the consumer product, and wherein the first surface of the polyolefin film forms an inner surface facing toward the consumer product. At least a portion of the first surface of the polyolefin film may be in contact with the consumer product or may be in contact with primary packaging of the consumer product. The polyolefin film may comprise more than one polyolefin layer, and the layer forming the first surface may be devoid of recycled polyolefin material.

Packages of the present disclosure may comprise a polyolefin film as described herein, wherein the first surface of the polyolefin film forms an outer surface of the package facing away from the consumer product, and wherein the second surface of the polyolefin film forms an inner surface facing toward the consumer product. At least a portion of the second surface of the polyolefin film may be in contact with the consumer product or may be in contact with primary packaging of the consumer product. The polyolefin film may comprise three polyolefin layers, wherein the layers forming the first surface and the second surface of the polyolefin film may be devoid of recycled polyolefin material, and the layer disposed between the layers forming the first surface and the second surface (the intermediate layer) may comprise recycled polyolefin material.

The consumer product at least partially enclosed by the package of the present disclosure may be any consumer product as defined herein. The consumer product may be an absorbent article, such as a diaper, as shown in FIG. 10, an absorbent pant, as shown in FIG. 11, a toilet paper roll, as shown in FIG. 12, or a paper towel roll, as shown in FIG. 13.

Figure 10:
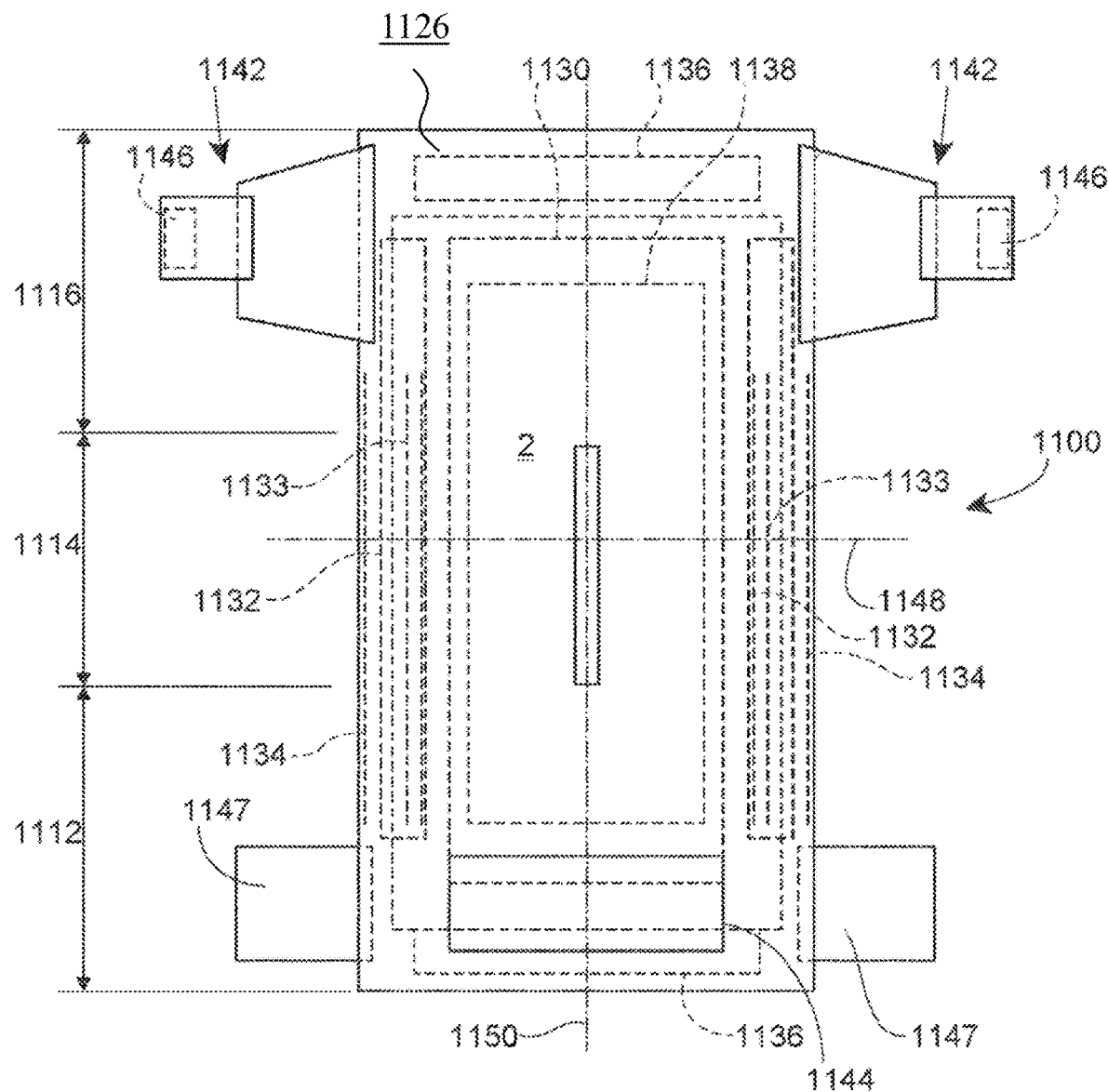
FIG. 10 is a plan view of an example absorbent article in the form of a diaper, garment-facing surface facing the viewer, in a flat laid-out state.
Figure 11:
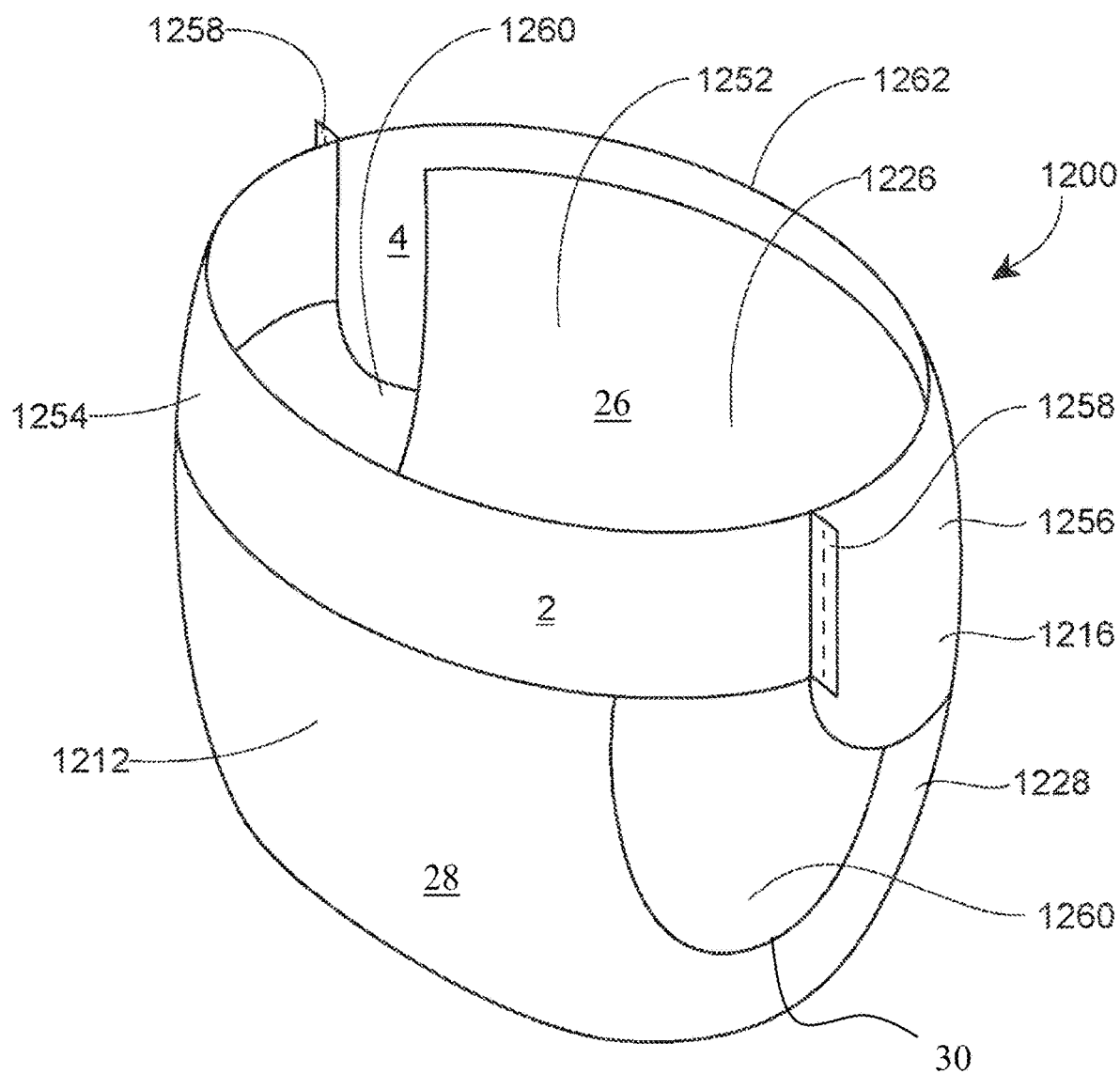
FIG. 11 is a front perspective view of an absorbent article in the form of a pant.

FIG. 10 shows a plan view of an example diaper 1100, garment-facing surface 2 facing the viewer in a flat, laid-out state (i.e., no elastic contraction). The diaper 1100 may comprise a front waist region 1112, a crotch region 1114, and a back waist region 1116. The crotch region 1114 may extend intermediate the front waist region 1112 and the back waist region 1116. The front wait region 1112, the crotch region 1114, and the back waist region 1116 may each be ⅓ of the length of the diaper 1110. The diaper 1110 may comprise a liquid permeable topsheet 1126, a liquid impermeable backsheet, and an absorbent core 1130 positioned at least partially intermediate the topsheet 1126 and the backsheet. The diaper 1110 may also comprise one or more pairs of barrier leg cuffs 1132 with or without elastics 1133, one or more pairs of leg elastics 1134, one or more elastic waistbands 1136, and/or one or more acquisition materials 1138. The acquisition material or materials 1138 may be positioned intermediate the topsheet 1126 and the absorbent core 1130. An outer cover material, such as a nonwoven material, may cover a garment-facing side of the backsheet. The diaper 1110 may comprise back ears 1142 in the back waist region 1116. The back ears 1142 may comprise fasteners 1146 and may extend from the back waist region 1116 of the diaper 1110 and attach (using the fasteners 1146) to the landing zone area or landing zone material 1144 on a garment-facing portion of the front waist region 1112 of the diaper 1110. The diaper 1110 may also have front ears 1147 in the front waist region 1112. The diaper 1110 may have a central lateral (or transverse) axis 1148 and a central longitudinal axis 1150. The central lateral axis 1148 extends perpendicular to the central longitudinal axis 1150. FIG. 11 shows a front perspective view of an absorbent article in the form of a pant 1200.

The pant 1200 may have a chassis 1252 (sometimes referred to as a central chassis or central panel) comprising a topsheet 1226, a backsheet 28, and an absorbent core 30 disposed at least partially intermediate the topsheet 26 and the backsheet 1228, and an optional acquisition material, similar to that as described above with respect to the diaper represented by FIG. 10. The pant 1200 may comprise a front belt 1254 in the front waist region 1212 and a back belt 1256 in the back waist region 1216. The chassis 1252 may be joined to a wearer-facing surface 4 of the front and back belts 1254, 1256 or to a garment-facing surface 2 of the belts 1254, 1256. Side edges of the front belt 1254 may be joined to side edges of the back belt 1256 to form two side seams 1258. The side seams 1258 may be any suitable seams known to those of skill in the art, such as butt seams or overlap seams, for example. When the side seams 1258 are permanently formed or refastenably closed, the pant 1200 in the form of a pant has two leg openings 1260 and a waist opening circumference 1262. The side seams 1258 may be permanently joined using adhesives or bonds, for example, or may be refastenably closed using hook and loop fasteners, for example.

Figure 12:
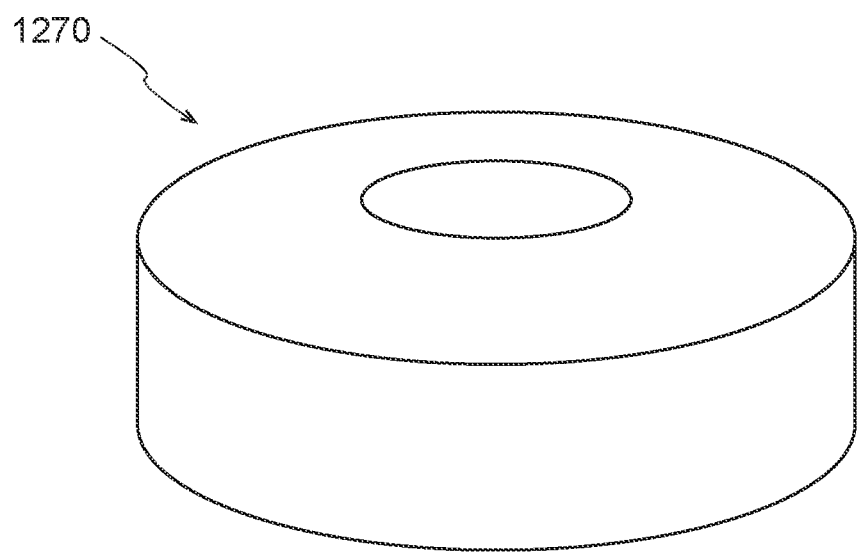
FIG. 12 is a perspective view of a consumer product in the form of a toilet paper roll.
Figure 13:
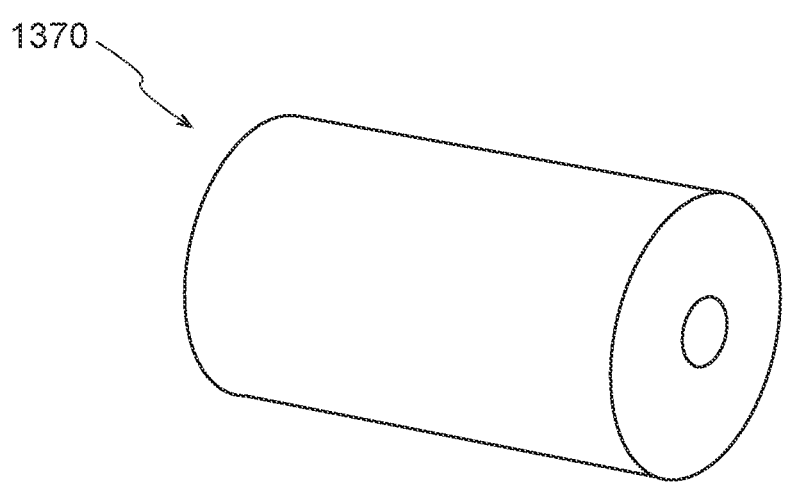
FIG. 13 is a perspective view of a consumer product in the form of a paper towel roll.

FIG. 12 shows a perspective view of a toilet paper roll 1270 that may be disposed at least partially within the package of the present disclosure. The toilet paper roll 1270 may be completely enclosed within the package of the present disclosure.

FIG. 13 shows a perspective view of a paper towel roll 1370 that may be disposed at least partially within the package of the present disclosure. The paper towel roll 1370 may be completely enclosed within the package of the present disclosure.

The packages of the present disclosure may comprise a plurality of compressed consumer products, e.g., compressed absorbent articles. For example, packages of the present disclosure may be used for accommodating diapers. Referring again to FIG. 9, the package 1000 defines an interior space 1002 in which a plurality of absorbent articles 1004 are situated. The plurality of absorbent articles 1004 may be arranged in one or more stacks 1006. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages.

Accordingly, packages of the consumer products, such as absorbent articles, of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

It is worth noting that the consumer products within the packages of the present disclosure can be arranged in a myriad of configurations. For example, absorbent articles of the present disclosure may be disposed within the package such that they are oriented in a vertical orientation, or the absorbent articles may be arranged such that they are arranged in a horizontal configuration, for example as shown in FIG. 9. Forms are contemplated where a combination of horizontal and vertically oriented articles are provided in the package.

High-Custody Sourcing Method

Figure 14:
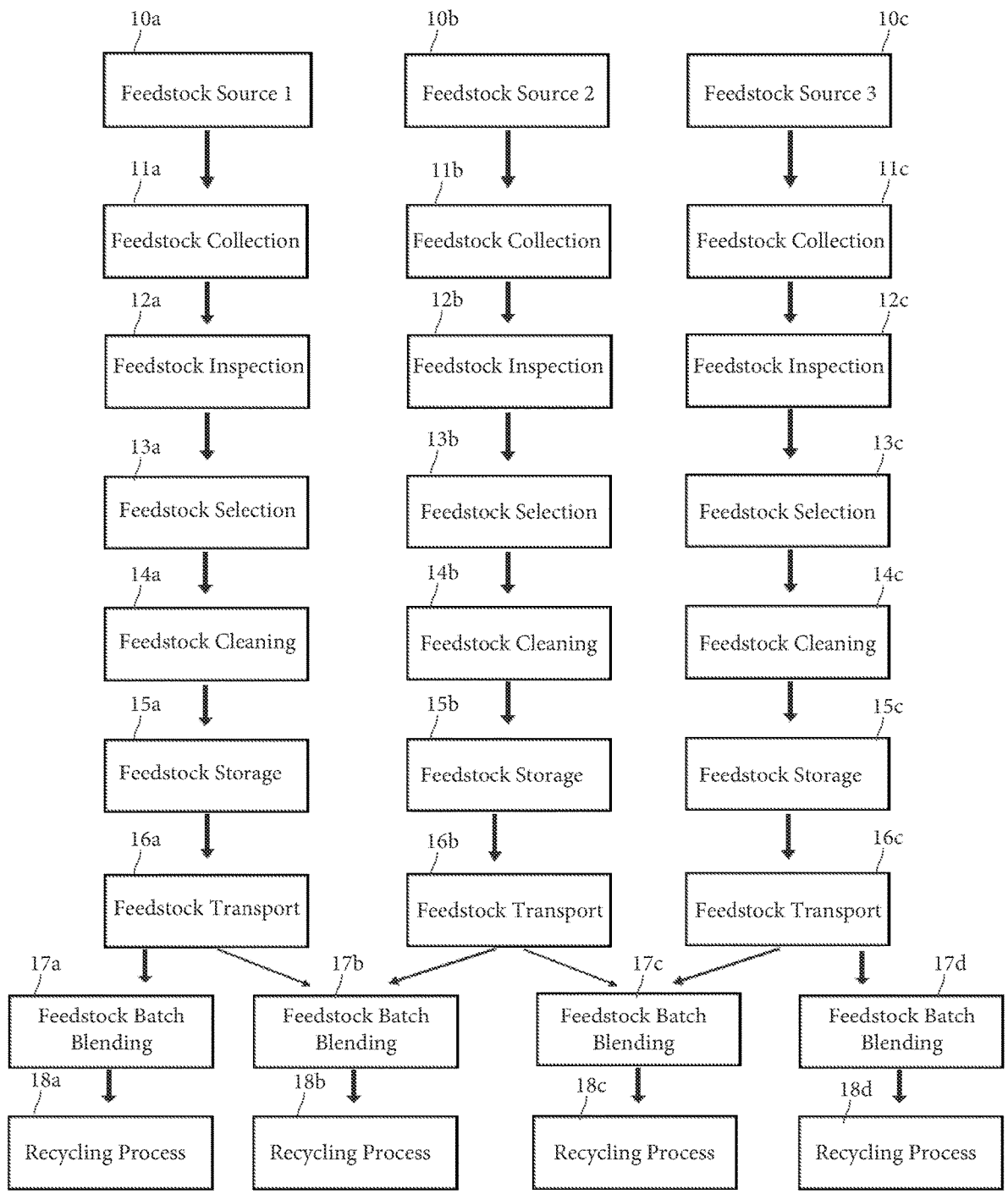
FIG. 14 is a process flow diagram of the high-custody sourcing method described herein

The recycled polyolefin material of the present disclosure may be obtained from a high-custody sourcing method. The high-custody sourcing method of the present disclosure is configured to deliver high purity recycled polyolefin material that may be incorporated at significant levels into a polyolefin film of the present disclosure. The high-custody sourcing method may allow for the increased incorporation of post-consumer polyolefin material into a finished polyolefin film that exhibits acceptable physical and chemical properties. Referring to FIG. 14, the high custody sourcing method may source feedstock recycled polyolefin material, including PIPM, PCPM, and combinations thereof, from a single feedstock source, such as Feedstock Source 1 10a, or may source feedstock recycled polyolefin material from multiple feedstock sources, such as Feedstock Source 2 10b and/or Feedstock Source 3 10c, in addition to Feedstock Source 1 10a. Feedstock sources may be distribution centers, supermarkets, packaging material manufacturers, film and/or polyolefin resin manufacturers, food-producing plants, consumer product-producing plants, agricultural operations, and the like. Feedstock recycled polyolefin material may be collected (feedstock collection 11a, 11b, 11c) by any means known in the art, such as segregation of like materials by use of indicia, such as recycling codes, on feedstock materials.

Feedstock recycled polyolefin material may be inspected (feedstock inspection 12a, 12b, 12c) by one or more methods designed to detect contamination, or the presence of materials other than the polyolefin material. Feedstock inspection 12a, 12b, 12c may be by visual inspection of feedstock recycled polyolefin material. Metal detection may be used as a method of feedstock inspection 12a, 12b, 12c in order to detect metal-containing contaminants in the recycled polyolefin material feedstock. Feedstock inspection 12a, 12b, 12c may also be by computer image analysis of feedstock recycled polyolefin material. Analysis of images of feedstock recycled polyolefin material by computer software may be used to detect contaminants in the feedstock material.

Feedstock selection 13a, 13b, 13c may comprise manual selection of feedstock recycled polyolefin material and/or automated selection of feedstock recycled polyolefin material based on results from the feedstock inspection step 12a, 12b, 12c. Automated equipment may be configured to select and/or deselect individual pieces or portions of feedstock recycled polyolefin material based on inspection results.

Feedstock cleaning 14a, 14b, 14c may be configured to remove contaminants, foreign material, and/or other materials that are not polyolefin material, such as paper and/or metalized labels, ink, dirt, product, and the like. Feedstock cleaning 14a, 14b, 14c may comprise exposure of the feedstock recycled polyolefin material to a source or sources of high-velocity air, streams and/or jets of water, surfactant-containing compositions, solvent-containing compositions, mechanical abrasion, and combinations thereof.

Feedstock storage 15a, 15b, 15c may comprise steps designed to maintain the clean state of the cleaned feedstock recycled polyolefin material and/or prevent or at least reduce recontamination. Feedstock storage 15a, 15b, 15c may comprise the placement of feedstock recycled polyolefin material under certain environmental controls. In a form, feedstock storage may comprise the placement of the feedstock material under temperature controls in order to prevent or minimize exposure to extreme high or low temperatures. Temperature control may be beneficial to prevent or inhibit the development of undesirable components due to the exposure of polyolefin material to extreme temperatures. In another form, feedstock storage may comprise the placement of the feedstock material under humidity controls in order to prevent or minimize exposure to extreme high or low humidity conditions. In yet another form, feedstock storage may comprise the placement of the feedstock material under cover to provide a physical barrier to environmental contaminants, such as dirt, water, and dust.

Feedstock transport 16a, 16b, 16c may comprise transport of the feedstock recycled polyolefin material from one location to another in a manner designed to prevent or reduce contamination. Feedstock transport 16a, 16b, 16c may comprise transport of the feedstock material within dedicated containers and/or dedicated vehicles. Dedicated containers and dedicated vehicles may be used only for the transport of high-custody sourced feedstock recycled polyolefin material. Dedicated containers and dedicated vehicles may be cleaned between each exposure of feedstock material. Feedstock transport 16a, 16b, 16c may comprise transport of the feedstock material within closed containers and/or closed vehicles. In a form, feedstock transport 16a, 16b, 16c may comprise transport of feedstock material in dedicated, closed containers and/or dedicated, closed vehicles.

Feedstock batch blending 17a, 17b, 17c, 17d may comprise a step or steps designed to produce dedicated lots of recycled polyolefin material, maintain traceability of dedicated lots, and/or balance properties of feedstock material over lots to produce a consistent recycled polyolefin material for incorporation into the polyolefin films of the present disclosure. Feedstock batch blending 17a-17d may comprise selection of amounts of feedstock material from one or more feedstock sources for batch blending based on physical, chemical, or other properties that are believed to produce the desired recycled polyolefin material to be incorporated into the polyolefin films of the present disclosure. Feedstock batch blending 17a-17d may comprise identification and recordation of source feedstock materials blended together, assignment of unique batch/lot identifiers, and maintenance of source and batch/lot records.

Recycling process 18a, 18b, 18c 18d may comprise the creation of recycled polyolefin material from the feedstock recycled polyolefin material. The recycling process 18a-18d is designed to produce recycled polyolefin material with acceptable physical and chemical properties. The recycling process 18a-18d may comprise identification of one or more unique batches/lots of blended feedstock material. Selection may be designed to balance certain physical, chemical, or other properties that are believed to produce the desired recycled polyolefin material to be incorporated into the polyolefin films of the present disclosure. The recycling process 18a-18d may comprise recordation and maintenance of batch/lot information to enable traceability of the final recycled polyolefin material back to the original feedstock material(s) and/or source(s). The recycling process 18a-18d may comprise cleaning protocols designed to reduce or eliminate contamination of the recycled polyolefin material. The recycling process 18a-18d may comprise principles of Good Manufacturing Practices (GMP).

EXAMPLES

Examples 1-22, presented in Table 1, are contemplated examples of the polyolefin films of the present disclosure. The total caliper of each of examples 1-22 is contemplated to be between about 30 μm and about 100 μm. Examples 1-7 are monolayer polyolefin films comprising a single polyolefin layer. Example 8 is a multilayer polyolefin film comprising two layers. Examples 9-22 are multilayer polyolefin films comprising three layers.

TABLE 1

|  | Intermediate/ Only Layer | First Layer | Second Layer | Total Recycled Polyolefin (%) |
|---|---|---|---|---|
| Example 1 | 65%-75% virgin LDPE/25%-35% recycled polyolefin | — | — | 25-35 |
| Example 2 | 60%-74% virgin LDPE/25%-35% recycled polyolefin/1%-5% additive(s) | — | — | 25-35 |
| Example 3 | 57%-74% virgin LLDPE/25%-35% recycled polyolefin/1%-8% additive(s) | — | — | 25-35 |
| Example 4 | 57%-74% virgin MDPE/25%-35% recycled polyolefin/1%-8% additive(s) | — | — | 25-35 |
| Example 5 | 50%-64% virgin HDPE/36%-50% recycled polyolefin | — | — | 36-50 |
| Example 6 | 50%-64% virgin LDPE/36%-50% recycled polyolefin | — | — | 36-50 |
| Example 7 | 42%-63% virgin LDPE/36%-50% recycled polyolefin/1%-8% additive(s) | — | — | 36-50 |
| Example 8 | — | 60%-70% of film (30%-71% virgin LDPE/29%-68% recycled polyolefin/0%-10% additive(s)) | 30%-40% of film (90%-100% virgin LLDPE/0%-10% additive(s)) | 17.4-48 |
| Example 9 | 40%-60% of film (0%-50% virgin LDPE/50%-100% recycled polyolefin/0%-10% additive(s)) | 20%-30% of film (90%-100% virgin LLDPE/0%-10% additive(s)) | 20%-30% of film (90%-100% virgin LLDPE/0%-10% additive(s)) | 20-60 |
| Example 10 | 40%-60% of film (0%-50% virgin MDPE/50%-100% recycled polyolefin/0%-10% additive(s)) | 20%-30% of film (90%-100% virgin LLDPE/0%-10% additive(s)) | 20%-30% of film (90%-100% virgin LLDPE/0%-10% additive(s)) | 20-60 |
| Example 11 | 40%-60% of film (0%-90% virgin LDPE/10%-100% recycled polyolefin/0%-10% additive(s)) | 20%-30% of film (0%-100% virgin LLDPE/0%-100% recycled polyolefin/0%-10% additive(s)) | 20%-30% of film (90%-100% virgin LLDPE/0%-10% additive(s)) | 10-60 |
| Example 12 | 40%-60% of film (0%-% virgin LDPE/50%-100% recycled polyolefin/0%-10% additive(s)) | 20%-30% of film (0%-100% virgin LLDPE/0%-100% recycled polyolefin/0%-10% additive(s)) | 20%-30% of film (90%-100% virgin LLDPE/0%-10% additive(s)) | 20-60 |
| Example 13 | 40%-60% of film (0%-% virgin LDPE/50%-100% recycled polyolefin/0%-10% additive(s)) | 20%-30% of film (0%-100% virgin LLDPE/0%-100% recycled polyolefin/0%-10% additive(s)) | 20%-30% of film (90%-100% virgin LLDPE/0%-10% additive(s)) | 20-60 |
| Example 14 | 40%-60% of film (0%-% virgin MDPE/50%-100% recycled polyolefin/0%-10% additive(s)) | 20%-30% of film (0%-100% virgin LLDPE/0%-100% recycled polyolefin/0%-10% additive(s)) | 20%-30% of film (90%-100% virgin LLDPE/0%-10% additive(s)) | 20-60 |

TABLE 1-continued

| | Intermediate/ Only Layer | First Layer | Second Layer | Total Recycled Polyolefin (%) |
|---|---|---|---|---|
| Example 15 | 40%-60% of film (0%-49% virgin LDPE/50%-99% recycled polyolefin/1%-10% additive(s)) | 20%-30% of film (0%-96.7% virgin LLDPE/3.3%-100% recycled polyolefin) | 20%-30% of film (100% virgin LLDPE) | 40-60 |
| Example 16 | 40%-60% of film (0%-79% virgin LDPE/20%-99% recycled polyolefin/1%-10% additive(s)) | 20%-30% of film (0%-95% virgin LLDPE/5%-100% recycled polyolefin) | 20%-30% of film (0%-95% virgin LLDPE/5%-100% recycled polyolefin) | 40-95 |
| Example 17 | 40%-60% of film (0%-74% virgin LDPE/25%-99% recycled polyolefin/1%-10% additive(s)) | 20%-30% of film (5%-95% virgin LLDPE/5%-95% recycled polyolefin) | 20%-30% of film (5%-100% virgin LLDPE/5%-95% recycled polyolefin) | 40-95 |
| Example 18 | 40%-60% of film (0%-69% virgin LDPE/30%-99% recycled polyolefin/1%-10% additive(s)) | 20%-30% of film (25%-95% virgin LLDPE/5%-75% recycled polyolefin) | 20%-30% of film (5%-95% virgin LLDPE/5%-95% recycled polyolefin) | 40-95 |
| Example 19 | 40%-60% of film (0%-69% virgin LDPE/30%-99% recycled polyolefin/1%-10% additive(s)) | 20%-30% of film (25%-95% virgin LLDPE/5%-75% recycled polyolefin) | 20%-30% of film (5%-95% virgin LLDPE/5%-95% recycled polyolefin) | 40-94 |
| Example 20 | 40%-60% of film (0%-64% virgin LDPE/35%-99% recycled polyolefin/1%-10% additive(s)) | 20%-30% of film (25%-95% virgin LLDPE/5%-75% recycled polyolefin) | 20%-30% of film (25%-95% virgin LLDPE/5%-75% recycled polyolefin) | 30-90 |
| Example 21 | 40%-60% of film (0%-69% virgin LDPE/30%-99% recycled polyolefin/1%-10% additive(s)) | 20%-30% of film (50%-95% virgin LLDPE/5%-50% recycled polyolefin) | 20%-30% of film (50%-95% virgin LLDPE/5%-50% recycled polyolefin) | 25-80 |
| Example 22 | 60%-80% of film (0%-74% virgin LDPE/25%-99% recycled polyolefin/1%-15% additive(s)) | 10%-20% of film (50%-100% virgin LLDPE/0%-50% recycled polyolefin) | 10%-20% of film (50%-100% virgin LLDPE/0%-50% recycled polyolefin) | 15-90 |

Examples 23-25 and Comparative Example 1 are tested for trace chemical concentrations according to the Trace Chemicals Test Method described herein. The results are presented in Table 2.

Example 23 is a blend of 100% recycled post-consumer LDPE material obtained through a high-custody sourcing method.

Example 24 is the 100% recycled post-consumer LDPE resin material obtained through a high-custody sourcing method of example 24 after processing through mechanical recycling.

Example 25 is a polyolefin film comprising 50% of the post-consumer recycled polyolefin material of Example 24, and 50% virgin LDPE, with a total film thickness of 30 μm.

Comparative Example 1 is 100% recycled post-consumer polyolefin LDPE resin obtained from a conventional recycled material sourcing method.

TABLE 2

| Trace Chemical | Example 23 | Example 24 | Example 25 | Comparative Example 1 |
|---|---|---|---|---|
| Isononylphenol [μg/kg] | <LOQ | <LOQ | 75 | 3,400 |
| PCB 77 [ng/kg] | 3.19 | 41.9 | 19.6 | 77.2 |
| PCB 118 [ng/kg] | 29.5 | 138 | 84 | 2,500 |
| OCDD [ng/kg] | <LOQ | 0.335 | 0.641 | 50.5 |
| OCDF [ng/kg] | <LOQ | <LOQ | <LOQ | 2.22 |
| Bisphenol A [μg/kg] | <LOQ | 14 | <LOQ | 3,300 |
| Diisononyl phthalate [μg/kg] | <LOQ | <LOQ | <LOQ | 1,300 |

Table 3 shows that PCPM obtained through a high-custody sourcing method contain fewer and less trace chemicals as compared to PCPM obtained through conventional sourcing methods.

Example 26 is a polyolefin film comprising 56% post-consumer polyolefin resin material obtained through a high-custody sourcing method.

Comparative Example 2 is a 100% recycled post-consumer polyolefin LDPE film obtained from a conventional recycled material sourcing method.

TABLE 3

| Film Physical Properties | Example 26 | Comparative Example 2 |
|---|---|---|
| Average Gel Count | 17 | >25 |
| Average Gel Height (mm) | 16.9 | 51.3 |
| Average Relative Gel Height (%) | 23.7 | 73.3 |
| Average Spot Count | 0 | >2 |
| #Holes | 0 | 0 |

As shown in Table 3, polyolefin film comprising PCPM sourced from a high-custody sourcing method produces a film with significantly fewer gels, gels with a smaller profile, and significantly fewer dark spots. A film with fewer and lower-profile gels is less likely to encounter issues during printing, as gels may impair the printing process and may distort graphics printed on the film surface.

Test Methods

Gel Count Test Method

The Gel Count Test Method is used to quantify the incidence of defects of interest in sample packaging film of interest. Evaluation on several specimens of a sample packaging film is primarily done visually, and several output parameters relating to gels, dark spots, and holes are established.

Five like specimens, rectangular and 20 cm×20 cm, are taken from a sample packaging film of interest. If the film is available as roll stock, the five specimens are cut from one or more rolls of material, with material preferentially being taken from unprinted regions. If the packaging film of interest is not available in roll stock form and is, for example, only available as formed packaging bags for containing consumer products, these five specimens are extracted from one or more packaging bags. The surface of the film facing inward in the bag (i.e., toward and generally enveloping consumer products when the bag is loaded with product) is defined as the inner surface of the film and the surface of the film facing outward away from consumer products is defined as the outer surface of the film. In the case the specimens are taken from roll stock before bags are formed (and potentially before any printed step present in the film conversion process), if the surface intended to be an outer surface after conversion is known, this is considered to be the outer surface and the opposite surface is considered to be the inner surface. If the surface intended to be an outer surface is unknown, the outer surface is determined in the dark-spot-counting procedure as described below.

Each of the five film specimens is backlit by being placed on a white light box sequentially and viewed with the naked eye. For each of the five film specimens, any holes or tears apparent in the film are identified and marked. A hole may comprise a visually discernible area of film where the absence film mass is apparent. A tear may comprise a hole which has an elongated opening or absence of film mass extending in one direction. Any gels apparent are also identified and marked. (For the purposes of this method, a gel is a distinct individual entity, generally visually discernible and consistent with a small clump of cross-linked polymer resin or as defined elsewhere within this patent document.) A caliper gauge with flat, round foot 6.00 to 6.25 mm in diameter and exerting less than 3.5 N of force is used to measure and record the absolute height of each gel to the nearest 0.01 mm. One example of a suitable apparatus is caliper gauge model ID-C112BS available from Mitutoyo Corporation, Kawasaki, Japan, or equivalent. For each gel, the caliper of proximal, well-formed film is also measured in like fashion. For each gel, its gel height is defined as gel height [mm]=absolute height of gel [mm]−proximal film caliper [mm]

and its relative gel height, in percent, is defined as $$\text{relative gel height } [\%] = \frac{\text{gel height [mm]}}{\text{proximal film caliper [mm]}} \times 100\%.$$

For each gel, the gel height and relative gel height are measured, calculated, and recorded. If a cluster of gels containing individually discernible gels spaced so closely such that the caliper gauge cannot measure the height of each gel individually, the gel height and relative gel height of the tallest gel in the cluster is assigned to all gels in the cluster.

Each surface of each of the five film specimens is then viewed by the naked eye front-lit under diffuse white light, and any dark specs or spots are identified and counted. For specimens of sample film for which the inner surface and outer surface are not known, the surface with the greater number of spots is considered the inner surface. For specimens of sample film for which the inner surface and outer surface is known, the number of dark specs or spots are counted as appearing on the inner surface or the outer surface depending which is being viewed.

For the sample film evaluated via the five specimens, the Average Hole Count is defined as the total number of holes observed among the five specimens divided by five and is reported to the nearest tenth. The Average Gel Count is defined as the total number of gels observed among the five specimens divided by five and reported to the nearest tenth. The Average Gel Height is the arithmetic mean among all gel heights recorded, reported to the nearest 0.002 mm. The Average Relative Gel Height is the arithmetic mean among all relative gel heights recorded and is reported to the nearest 0.1%. The Average Inner-Surface Spot Count is the total number of dark specs or spots observed on the inner surface of the five specimens divided by five and reported to the nearest tenth. The Average Outer-Surface Spot Count is the total number of dark specs or spots observed on the outer surface of the five specimens divided by five and reported to the nearest tenth. The Average Total Spot Count is the sum of the Average Inner-Surface Spot Count and the Average Outer-Surface Spot Count and is reported to the nearest tenth.

Trace Chemicals Test Method

The content on a mass per mass basis of trace chemicals present in packaging film or recycled polyolefin material is determined using methods containing sample extraction and instrumental analysis approaches known of those of skill in the art and understood to be capable of extracting and detecting essentially all of a particular trace chemical in packaging film. Suitable overall method specifics vary based on the particular trace chemical being quantified, though a common overall method structure is generally followed. A suitable method generally begins with increasing the surface area of a representative packaging film or recycled polyolefin material sample by cutting, shredding, and/or milling into small particles. An extraction step is then performed using a solvent capable of dissolving or diffusing into the polymer sample and in which the trace chemical is readily soluble. The extraction process conditions (e.g., time and temperature) are optimized to maximize trace chemical recovery and common approaches include but are not limited to Soxhlet extraction, accelerated solvent extraction, and/or ultrasonic extraction. Internal standards (usually stable-isotope-labeled versions of the trace chemicals if mass spectrometry-based detection approaches are used) are added during the extraction step to account for potential losses during extraction and subsequent processing steps. After extraction is complete, the extraction solvent is isolated and worked up for instrumental analysis. Depending on the solvent used for extraction, the required quantitation limit, and the specific instrumental approach used, generation of a specimen suitable for instrumental analysis may require multiple cleanup and/or concentration steps including but not limited to centrifugation/filtration, liquid/liquid extraction, and/or column chromatography. The trace chemical in the worked-up specimen is then quantified using instrumental methods (e.g., GC-MS, GC-MS/MS, GC-HRMS, LC-MS/MS, etc.) known to those of skill in the art and specifically adapted to the trace chemical of interest. Suitable instrumental approaches may be developed de novo or may be based on standard, known methods for particular trace chemicals (e.g., US EPA Method 1613 in the case of dioxins and furans or US EPA 1668 for PCBs). Based on a combination of raw instrumental quantitative results, extraction solvent workup steps, original extraction volume, and starting specimen mass, the mass content of a trace chemical per mass of starting specimen material is calculated and is reported as the level of the trace chemical in the packaging film tested. Given the generally low levels of trace chemicals present, common units used in reported levels of trace chemicals are µg/kg and ng/kg (equivalent to the ppb and ppt levels, respectively).

One of skill in the art will recognize that trace chemicals are often present at very low "trace" levels, meaning that under some circumstances, environmental and/or laboratory background levels of these same trace chemicals may give rise to false positive detects or falsely elevated results if appropriate precautions are not taken. While one of skill in the art recognizes that a suite of measures may be needed to minimize such false results, one obligatory measure is to include a true "blank" beginning with solvent carried in parallel through the extraction step, extraction solvent workup, and instrumental analysis.

Using the suitable overall methodology outlined above, one of skill in the art may quantify a range of trace chemicals potentially present in a packaging film or recycled polyolefin material sample of interest. For example, the level of isononylphenol (CAS RN 11066-49-2) may be determined and reported as mass of trace chemical per mass of packaging film or recycled polyolefin material in units of µg/kg. Similarly, the level of PCB 77 (CAS RN 32598-13-3) may be determined and reported in units of ng/kg, the level of PCB 118 (CAS RN 31508-00-6) may be determined and reported in units of ng/kg, the level of OCDD (CAS RN 3268-87-9), a dioxin, may be determined and reported in units of ng/kg, the level of OCDF (CAS RN 39001-02-0), a furan, may be determined and reported in units of ng/kg, the level of bisphenol A (CAS RN 80-05-7), also known as BPA, may be determined and reported in units of µg/kg, and the level of diisononyl phthalate (CAN RN 28553-12-0), also known as DINP, may be determined and reported in units of µg/kg.

In-Bag Stack Height Test

The in-bag stack height of a package of absorbent articles is determined as follows:

Equipment:

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure:

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 3). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Combinations

1. A package comprising:
   a polyolefin film, and
   a consumer product;
   wherein the polyolefin film comprises a first surface and a second surface;
   wherein the polyolefin film comprises between about 10% and about 95%, between about 25% and about 95%, between about 30% and about 95%, between about 40% and about 95%, or between about 50% and about 95%, by weight of the polyolefin film, of recycled polyolefin;
   wherein the polyolefin film has an Average Hole Count between about 0.0 and about 10.0, or between about 0.0 and about 8.0, or between about 0.0 and about 5.0, or between about 0.0 and about 3.0, according to the Gel Count Test Method;
   wherein the polyolefin film has an Average Gel Count between about 0.0 and about 100.0, between about 0.0 and about 50.0, between about 0.0 and about 25.0, or between about 0.0 and about 5.0, according to the Gel Count Test Method;

wherein the polyolefin film has an Average Relative Gel Height between about 0.0% and about 150.0%, between about 0.0% and about 125.0%, between about 0.0% and about 100.0%, between about 0.0% and about 75.0%, or between about 0.0% and about 50.0%, according to the Gel Count Test Method;

wherein the polyolefin film has a Total Spot Count between about 0.0 and about 100.0, between about 0.0 and about 50.0, between about 0.0 and about 25.0, or between about 0.0 and about 5.0, according to the Gel Count Test Method; and wherein the polyolefin film at least partially encloses the consumer product.

2. The package of paragraph 1, wherein the first surface of the polyolefin film comprises printed graphics.

3. The package of paragraph 1 or paragraph 2, wherein the second surface of the polyolefin film is devoid of printed graphics.

4. The package of any of the preceding paragraphs, wherein the first surface of the polyolefin film forms an outer surface facing away from the consumer product, and wherein the second surface of the polyolefin film forms an inner surface facing toward the consumer product.

5. The package of any of paragraphs 1-3, wherein the first surface of the polyolefin film forms an inner surface facing toward the consumer product, and wherein the second surface of the polyolefin forms an outer surface facing away from the consumer product.

6. The package of any of paragraphs 4 or 5, wherein the polyolefin film has an Inner Surface Spot Count between about 0.0 and about 100.0, or between about 0.0 and 50.0, or between about 0.0 and about 25.0, or between about 0.0 and about 5.0 and/or an Outer Surface Spot Count of between about 0.0 and about 100.0, or between about 0.0 and 50.0, or between about 0.0 and about 25.0, or between about 0.0 and about 5.0, according to the Gel Count Test Method.

7. The package of any of the preceding paragraphs, wherein the polyolefin film comprises less than 1,000 µg/kg, less than 500 µg/kg, less than 150 µg/kg, or less than 100 µg/kg of isononylphenol, according to the Trace Chemicals Test Method.

8. The package of any of the preceding paragraphs, wherein the polyolefin film comprises less than 75 ng/kg, less than 50 ng/kg, or less than 25 ng/kg of PCB 77, according to the Trace Chemicals Test Method.

9. The package of any of the preceding paragraphs, wherein the polyolefin film comprises less than 2,000 ng/kg, less than 1,000 ng/kg, less than 200 ng/kg, or less than 100 ng/kg of PCB 118, according to the Trace Chemicals Test Method.

10. The package of any of the preceding paragraphs, wherein the polyolefin film comprises less than 45.00 ng/kg, less than 25.00 ng/kg, less than 5.00 ng/kg, or less than 0.85 ng/kg of OCDD, according to the Trace Chemicals Test Method.

11. The package of any of the preceding paragraphs, wherein the polyolefin film comprises less than 1.8 ng/kg, less than 1.2 ng/kg, less than 0.8 ng/kg, or less than 0.2 ng/kg of OCDF, according to the Trace Chemicals Test Method.

12. The package of any of the preceding paragraphs, wherein the polyolefin film comprises less than 2,500 µg/kg, less than 1,000 µg/kg, less than 500 µg/kg, less than 100 µg/kg, less than 50 µg/kg, or less than 5 µg/kg of bisphenol A, according to the Trace Chemicals Test Method.

13. The package of any of the preceding paragraphs, wherein the polyolefin film comprises less than 1,000 µg/kg, less than 500 µg/kg, less than 100 µg/kg, or less than 50 µg/kg of diisononyl phthalate, according to the Trace Chemicals Test Method.

14. The package of any of the preceding paragraphs, wherein the recycled polyolefin comprises less than 10,000 µg/kg, less than 2,500 µg/kg, less than 750 µg/kg, less than 250 µg/kg, or less than 50 µg/kg of isononylphenol, according to the Trace Chemicals Test Method.

15. The package of any of the preceding paragraphs, wherein the recycled polyolefin comprises less than 750 ng/kg, less than 500 ng/kg, less than 200 ng/kg, or less than 50 ng/kg of PCB 77, according to the Trace Chemicals Test Method.

16. The package of any of the preceding paragraphs, wherein the recycled polyolefin comprises less than 20,000 ng/kg, less than 10,000 ng/kg, less than 1,000 ng/kg, or less than 150 ng/kg of PCB 118, according to the Trace Chemicals Test Method.

17. The package of any of the preceding paragraphs, wherein the recycled polyolefin comprises less than 450.0 ng/kg, less than 250.0 ng/kg, less than 50.0 ng/kg, less than 5.0 mg/kg, or less than 0.5 ng/kg of OCDD, according to the Trace Chemicals Test Method.

18. The package of any of the preceding paragraphs, wherein the recycled polyolefin comprises less than 18 ng/kg, less than 10 ng/kg, less than 5 ng/kg, or less than 0.4 ng/kg of OCDF, according to the Trace Chemicals Test Method.

19. The package of any of the preceding paragraphs, wherein the recycled polyolefin comprises less than 25,000 µg/kg, less than 10,000 µg/kg, less than 5,000 µg/kg, less than 1,000 µg/kg, less than 500 µg/kg, less than 50 µg/kg, or less than 20 µg/kg of bisphenol A, according to the Trace Chemicals Test Method.

20. The package of any of the preceding paragraphs, wherein the recycled polyolefin comprises less than 5,000 µg/kg, less than 1,000 µg/kg, less than 500 µg/kg, or less than 50 µg/kg of diisononyl phthalate, according to the Trace Chemicals Test Method.

21. The package of any of the preceding paragraphs, wherein the recycled polyolefin comprises post-consumer polyolefin resin.

22. The package of paragraph 21, wherein the post-consumer polyolefin resin is obtained from a high-custody sourcing method.

23. The package of any of paragraphs 1-20, wherein the recycled polyolefin consists of post-consumer polyolefin resin.

24. The package of paragraph 23, wherein the post-consumer polyolefin resin is obtained from a high-custody sourcing method.

25. The package of any of the preceding paragraphs, wherein the consumer product comprises at least one of: diapers, wipes, absorbent pants, paper towel, toilet paper, facial tissue, and absorbent underwear.

26. A package comprising:
   a polyolefin film, and
   a consumer product disposed within the polyolefin film;
   wherein the polyolefin film comprises a first surface facing away from the consumer product and a second surface facing toward the consumer product;
   wherein the polyolefin film comprises between about between about 10% and about 95%, between about 25% and about 95%, between about 30% and about 95%, between about 40% and about 95%, or between about 50% and about 95%, by weight of the polyolefin film, of recycled polyolefin, wherein the recycled polyolefin comprises post-consumer polyolefin resin;
   wherein the polyolefin film has an Average Hole Count less than 10.0, less than 8.0, less than 5.0, or less than 3.0 according to the Gel Count Test Method;
   wherein the polyolefin film has an Average Gel Count less than 100.0, less than 50.0, less than 25.0, or less than 5.0, according to the Gel Count Test Method;
   wherein the polyolefin film has a Total Spot Count of less than 100.0, less than 50.0, less than 25.0, or less than 5.0, according to the Gel Count Test method; and
   wherein the polyolefin film comprises less than 1,000 µg/kg, less than 500 µg/kg, less than 150 µg/kg, or less than 100 µg/kg of isononylphenol, according to the Trace Chemicals Test Method.

27. The package of paragraph 26, wherein the polyolefin film comprises less than 75 ng/kg, less than 50 ng/kg, or less than 25 ng/kg of PCB 77, according to the Trace Chemicals Test Method.

28. The package of any of paragraphs 26 or 27, wherein the polyolefin film comprises less than 2,000 ng/kg, less than 1,000 ng/kg, less than 200 ng/kg, or less than 100 ng/kg of PCB 118, according to the Trace Chemicals Test Method.

29. The package of any of paragraphs 26-28, wherein the polyolefin film comprises less than 45.00 ng/kg, less than 25.00 ng/kg, less than 5.00 ng/kg, or less than 0.85 ng/kg of OCDD, according to the Trace Chemicals Test Method.

30. The package of any of paragraphs 26-29, wherein the polyolefin film comprises less than 1.8 ng/kg, less than 1.2 ng/kg, less than 0.8 ng/kg, or less than 0.2 ng/kg of OCDF, according to the Trace Chemicals Test Method.

31. The package of any of paragraphs 26-30, wherein the polyolefin film comprises less than 2,500 µg/kg, less than 1,000 µg/kg, less than 500 µg/kg, less than 100 µg/kg, less than 50 µg/kg, or less than 5 µg/kg of bisphenol A, according to the Trace Chemicals Test Method.

32. The package of any of paragraphs 26-31, wherein the polyolefin film less than 1,000 µg/kg, less than 500 µg/kg, less than 100 µg/kg, or less than 50 µg/kg of diisononyl phthalate, according to the Trace Chemicals Test Method.

33. The package of any of paragraphs 26-32, wherein the polyolefin film has an Average Gel Height of about 0.00 mm to about 150.00 mm, or of about 0.00 to about 90.00 mm, or of about 0.00 mm to about 60.00 mm, or of about 0.00 mm to about 45.00 mm, or of about 0.00 mm to about 30.00 mm, according to the Gel Count Test Method.

34. The package of any of paragraphs 26-33, wherein the polyolefin film has an Average Relative Gel Height between about 0.0% and about 150.0%, between about 0.0% and about 125.0%, between about 0.0% and about 100.0%, between about 0.0% and about 75.0%, or between about 0.0% and about 50.0%, according to the Gel Count Test Method.

35. The package of any of paragraphs 26-34, wherein the recycled polyolefin consists of post-consumer polyolefin resin.

36. The package of any of paragraphs 26-35, wherein the post-consumer polyolefin resin is obtained from a high-custody sourcing method.

37. The package of any of paragraphs 26-36, wherein the consumer product comprises at least one of: diapers, wipes, absorbent pants, paper towel, toilet paper, facial tissue, and absorbent underwear.

38. A package comprising:
   a polyolefin film, and
   a consumer product;
   wherein the polyolefin film comprises a first surface facing away from the consumer product and a second surface facing toward the consumer product;
   wherein the polyolefin film comprises between about between about 10% and about 95%, between about 25% and about 95%, between about 30% and about 95%, between about 40% and about 95%, or between about 50% and about 95%, by weight of the polyolefin film, of recycled polyolefin;
   wherein the polyolefin film has an Average Hole Count of 1.0 or less, according to the Gel Count Test Method;
   wherein the polyolefin film has an Average Gel Count between about 0.0 and about 100.0, between about 0.0 and about 50.0, between about 0.0 and about 25.0, or between about 0.0 and about 5.0, according to the Gel Count Test Method;
   wherein the polyolefin film has a Total Spot Count between about 0.0 and about 100.0, between about 0.0 and about 50.0, between about 0.0 and about 25.0, or between about 0.0 and about 5.0, according to the Gel Count Test method;
   wherein the polyolefin film is disposed around and fully encloses the consumer product; and
   wherein the at least a portion of the second surface of the polyolefin film is in direct contact with the consumer product.

39. The package of paragraph 38, wherein the polyolefin film comprises at least one of:
   a) less than 1,000 µg/kg, less than 500 µg/kg, less than 150 µg/kg, or less than 100 µg/kg of isononylphenol, according to the Trace Chemicals Test Method;
   b) less than 75 ng/kg, less than 50 ng/kg, or less than 25 ng/kg of PCB 77, according to the Trace Chemicals Test Method;
   c) less than 2,000 ng/kg, less than 1,000 ng/kg, less than 200 ng/kg, or less than 100 ng/kg of PCB 118, according to the Trace Chemicals Test Method;
   d) less than 45 ng/kg, less than 25 ng/kg, less than 5 ng/kg, or less than 0.85 ng/kg of OCDD, according to the Trace Chemicals Test Method;
   e) less than 1.8 ng/kg, less than 1.2 ng/kg, less than 0.8 ng/kg, or less than 0.2 ng/kg of OCDF, according to the Trace Chemicals Test Method;
   f) less than 2,500 µg/kg, less than 1,000 µg/kg, less than 500 µg/kg, less than 100 µg/kg, less than 50 µg/kg, or less than 5 µg/kg of bisphenol A, according to the Trace Chemicals Test Method; and g) less than 1,000 µg/kg, less than 500 µg/kg, less than 100 µg/kg, or less than 50 µg/kg of diisononyl phthalate, according to the Trace Chemicals Test Method.

40. The package of paragraph 38 or paragraph 39, wherein the recycled polyolefin comprises post-consumer polyolefin resin.

41. The package of paragraph 40, wherein the post-consumer polyolefin resin is obtained from a high-custody sourcing method.

42. The package of any of paragraphs 38-41, wherein the consumer product is an absorbent article, and wherein the package has an in-bag stack height in the range of between about 70 mm to about 100 mm, according to the In-Bag Stack Height Test.

43. A package comprising:
   a polyolefin film, and
   a consumer product;
   wherein the polyolefin film comprises a first surface and a second surface, wherein the first surface forms an outer surface facing away from the consumer product, and wherein the second surface forms an inner surface facing toward the consumer product;
   wherein the polyolefin film comprises between about between about 10% and about 95%, between about 25% and about 95%, between about 30% and about 95%, between about 40% and about 95%, or between about 50% and about 95%, by weight of the polyolefin film, of recycled polyolefin;
   wherein the polyolefin film has an Average Hole Count of between about 0.0 and about 10.0, between about 0.0 and about 8.0, between about 0.0 and about 5.0, or between about 0.0 and about 3.0, according to the Gel Count Test Method;
   wherein the polyolefin film has an Average Gel Count between about 0.0 and about 100.0, between about 0.0 and about 50.0, between about 0.0 and about 25.0, or between about 0.0 and about 5.0, according to the Gel Count Test Method;
   wherein the polyolefin film has an Average Gel Height between about 0.00 mm and about 150.00 mm, between about 0.00 and about 90.00 mm, between about 0.00 mm and about 60.00 mm, between about 0.00 mm and about 45.00 mm, or between about 0.00 mm and about 30.00 mm, according to the Gel Count Test Method;
   wherein the polyolefin film has an Inner Surface Spot Count of between about 0.0 and about 100.0, or between about 0.0 and 50.0, or between about 0.0 and about 25.0, or between about 0.0 and about 5.0 and/or an Outer Surface Spot Count of between about 0.0 and about 100.0, or between about 0.0 and 50.0, or between about 0.0 and about 25.0, or between about 0.0 and about 5.0, according to the Gel Count Test Method; and
   wherein the polyolefin film at least partially encloses the consumer product.

44. The package of paragraph 43, wherein the first surface of the polyolefin film comprises printed graphics.

45. The package of paragraph 43 or paragraph 44, wherein the second surface of the polyolefin film is devoid of printed graphics.

46. The package of any of paragraphs 43-45, wherein the polyolefin film comprises at least one of:
   a) less than 1,000 µg/kg, less than 500 µg/kg, less than 150 µg/kg, or less than 100 µg/kg of isononylphenol, according to the Trace Chemicals Test Method;
   b) less than 75 ng/kg, less than 50 ng/kg, or less than 25 ng/kg of PCB 77, according to the Trace Chemicals Test Method;
   c) less than 2,000 ng/kg, less than 1,000 ng/kg, less than 200 ng/kg, or less than 100 ng/kg of PCB 118, according to the Trace Chemicals Test Method;
   d) less than 45 ng/kg, less than 25 ng/kg, less than 5 ng/kg, or less than 0.85 ng/kg of OCDD, according to the Trace Chemicals Test Method;
   e) less than 1.8 ng/kg, less than 1.2 ng/kg, less than 0.8 ng/kg, or less than 0.2 ng/kg of OCDF, according to the Trace Chemicals Test Method;
   f) less than 2,500 µg/kg, less than 1,000 µg/kg, less than 500 µg/kg, less than 100 µg/kg, less than 50 µg/kg, or less than 5 µg/kg of bisphenol A, according to the Trace Chemicals Test Method; and
   g) less than 1,000 µg/kg, less than 500 µg/kg, less than 100 µg/kg, or less than 50 µg/kg of diisononyl phthalate, according to the Trace Chemicals Test Method.

47. The package of any of paragraphs 43-46, wherein the recycled polyolefin comprises post-consumer polyolefin resin.

48. The package of paragraph 47, wherein the post-consumer polyolefin resin is obtained from a high-custody sourcing method.

49. The package of any of paragraphs 43-46, wherein the recycled polyolefin consists of post-consumer polyolefin resin.

50. The package of paragraph 49, wherein the post-consumer polyolefin resin is obtained from a high-custody sourcing method.

51. The package of any of paragraphs 43-50, wherein the consumer product comprises at least one of: diapers, wipes, absorbent pants, paper towel, toilet paper, facial tissue, and absorbent underwear.

52. The package of any of the previous paragraphs, wherein the polyolefin film is formed from two or more layers of polyolefin material.

53. The package of paragraph 52, wherein the two or more layers of polyolefin material comprises a first layer and a second layer, and wherein the first layer comprises recycled polyolefin.

54. The package of paragraph 53, wherein the second layer is free of recycled polyolefin.

55. The package of paragraph 53, further comprising a third layer, and wherein the second layer and the third layer are free of recycled polyolefin.

56. The package of any of paragraphs 1-22, 26-34, 38-48, and 52-55, wherein the recycled polyolefin comprises post-industrial polyolefin material.

57. The package of any of the previous paragraphs, wherein the recycled polyolefin comprises polyethylenes (including LLDPE, LDPE, MDPE, and/or HDPE), polypropylene-ethylene interpolymer and copolymers having at least one olefinic constituent, and any mixtures thereof.

58. A polyolefin film comprising a first surface and a second surface;
   wherein the polyolefin film comprises between about 10% and about 95%, by weight of the polyolefin film, of recycled polyolefin;
   wherein the polyolefin film has an Average Hole Count between about 0.0 and about 10.0, according to the Gel Count Test Method;

wherein the polyolefin film has an Average Gel Count between about 0.0 and about 100.0, according to the Gel Count Test Method;

wherein the polyolefin film has an Average Relative Gel Height between about 0.0% and about 150.0%; and wherein the polyolefin film has a Total Spot Count between about 0.0 and about 100.0, according to the Gel Count Test Method.

59. The polyolefin film of paragraph 58, wherein the first surface of the polyolefin film comprises printed graphics.

60. The polyolefin film of paragraph 58, wherein the second surface of the polyolefin film is devoid of printed graphics.

61. The polyolefin film of paragraph 58 having an Average Gel Height between about 0.00 mm and about 150.00 mm, according to the Gel Count Test Method 62. The polyolefin film of paragraph 58, comprising at least one of:
   a) less than 1,000 μg/kg of isononylphenol, according to the Trace Chemicals Test Method;
   b) less than 75 ng/kg of PCB 77, according to the Trace Chemicals Test Method;
   c) less than 2,000 ng/kg of PCB 118, according to the Trace Chemicals Test Method;
   d) less than 45 ng/kg of OCDD, according to the Trace Chemicals Test Method;
   e) less than 1.8 ng/kg of OCDF, according to the Trace Chemicals Test Method;
   f) less than 2,500 μg/kg of bisphenol A, according to the Trace Chemicals Test Method; and
   g) less than 1,000 μg/kg of diisononyl phthalate, according to the Trace Chemicals Test Method.

63. The polyolefin film of paragraph 58, wherein the recycled polyolefin comprises at least one of:
   a) less than 10,000 μg/kg of isononylphenol, according to the Trace Chemicals Test Method;
   b) less than 750 ng/kg of PCB 77, according to the Trace Chemicals Test Method;
   c) less than 20,000 ng/kg of PCB 118, according to the Trace Chemicals Test Method;
   d) less than 450.0 ng/kg of OCDD, according to the Trace Chemicals Test Method;
   e) less than 18 ng/kg of OCDF, according to the Trace Chemicals Test Method;
   f) less than 25,000 μg/kg of bisphenol A, according to the Trace Chemicals Test Method; and
   g) less than 5,000 μg/kg, according to the Trace Chemicals Test Method.

64. The polyolefin film of paragraph 58, wherein the recycled polyolefin comprises post-consumer polyolefin material.

65. The polyolefin film of paragraph 64, wherein the post-consumer polyolefin material is obtained from a high-custody sourcing method 66. The polyolefin film of paragraph 58, wherein the recycled polyolefin comprises post-industrial polyolefin material.

67. The polyolefin film of paragraph 58, wherein the recycled polyolefin consists of post-consumer material.

68. The polyolefin film of paragraph 67, wherein the post-consumer material is obtained from a high-custody sourcing method.

69. The polyolefin film of paragraph 58, wherein the recycled polyolefin comprises at least one of: LLDPE, LDPE, MDPE, HDPE, polypropylene-ethylene interpolymer and copolymers having at least one olefinic constituent, and mixtures thereof.

70. A package comprising the polyolefin film of paragraph 58, wherein the package at least partially encloses a consumer product.

71. The package of paragraph 70, wherein the first surface of the polyolefin film forms an outer surface facing away from the consumer product, and wherein polyolefin film has an Outer Surface Spot Count of between about 0.0 and about 100.0, according to the Gel Count Test Method.

72. The package of paragraph 70, wherein the second surface of the polyolefin film forms an inner surface facing toward the consumer product, and wherein the polyolefin film has an Inner Surface Spot Count of between about 0.0 and about 100.0, according to the Gel Count Test Method.

73. The package of paragraph 70, wherein the consumer product is paper towels or toilet paper.

74. The package of paragraph 70, wherein the consumer product is an absorbent article.

75. The package of paragraph 74, wherein the package has an in-bag stack height in the range of between about 70 mm to about 100 mm, according to the In-Bag Stack Height Test.

76. The package of paragraph 74, wherein the absorbent article is a diaper or an absorbent pant.

77. The package of paragraph 74, wherein the absorbent article is a sanitary napkin.

78. The package of paragraph 70, wherein at least a portion of the package is in direct contact with the consumer product.

79. A package comprising the polyolefin film of paragraph 58, wherein the package at least partially encloses a good other than a consumer product.

80. The package of paragraph 79, wherein at least a portion of the package is in direct contact with the good other than a consumer product.

81. An overwrap formed from the polyolefin film of paragraph 58, wherein the overwrap is disposed proximate to an exterior surface of a primary package.

82. A polyolefin film comprising a first surface and a second surface;
   wherein the polyolefin film comprises between about 35% and about 95%, by weight of the polyolefin film, of recycled polyolefin;
   wherein the polyolefin film has an Average Hole Count between about 0.0 and about 10.0, according to the Gel Count Test Method;
   wherein the polyolefin film has an Average Gel Count between about 0.0 and about 100.0, according to the Gel Count Test Method;
   wherein the polyolefin film has an Average Relative Gel Height between about 0.0% and about 150.0%; and
   wherein the polyolefin film has a Total Spot Count between about 0.0 and about 100.0, according to the Gel Count Test Method.

83. The polyolefin film of paragraph 82, comprising at least one of:
   a) less than 1,000 μg/kg of isononylphenol, according to the Trace Chemicals Test Method;
   b) less than 75 ng/kg of PCB 77, according to the Trace Chemicals Test Method;
   c) less than 2,000 ng/kg of PCB 118, according to the Trace Chemicals Test Method;

d) less than 45 ng/kg of OCDD, according to the Trace Chemicals Test Method;
e) less than 1.8 ng/kg of OCDF, according to the Trace Chemicals Test Method;
f) less than 2,500 μg/kg of bisphenol A, according to the Trace Chemicals Test Method; and
g) less than 1,000 μg/kg of diisononyl phthalate, according to the Trace Chemicals Test Method.

84. A package comprising the polyolefin film of paragraph 83, wherein the package at least partially encloses a consumer product.

85. A package comprising:
a polyolefin film, and
a consumer product;
wherein the polyolefin film comprises a first surface and a second surface;
wherein the polyolefin film comprises between about 10% and about 95%, between about 25% and about 95%, between about 30% and about 95%, between about 40% and about 95%, or between about 50% and about 95%, by weight of the polyolefin film, of recycled polyolefin;
wherein the polyolefin film comprises at least one of:
a) less than 1,000 μg/kg, less than 500 μg/kg, less than 150 μg/kg, or less than 100 μg/kg of isononylphenol, according to the Trace Chemicals Test Method;
b) less than 75 ng/kg, less than 50 ng/kg, or less than 25 ng/kg of PCB 77, according to the Trace Chemicals Test Method;
c) less than 2,000 ng/kg, less than 1,000 ng/kg, less than 200 ng/kg, or less than 100 ng/kg of PCB 118, according to the Trace Chemicals Test Method;
d) less than 45 ng/kg, less than 25 ng/kg, less than 5 ng/kg, or less than 0.85 ng/kg of OCDD, according to the Trace Chemicals Test Method;
e) less than 1.8 ng/kg, less than 1.2 ng/kg, less than 0.8 ng/kg, or less than 0.2 ng/kg of OCDF, according to the Trace Chemicals Test Method;
f) less than 2,500 μg/kg, less than 1,000 μg/kg, less than 500 μg/kg, less than 100 μg/kg, less than 50 μg/kg, or less than 5 μg/kg of bisphenol A, according to the Trace Chemicals Test Method; and
g) less than 1,000 μg/kg, less than 500 μg/kg, less than 100 μg/kg, or less than 50 μg/kg of diisononyl phthalate, according to the Trace Chemicals Test Method; and wherein the polyolefin film at least partially encloses the consumer product.

86. A package comprising:
a polyolefin film, and
a consumer product;
wherein the polyolefin film comprises a first surface and a second surface;
wherein the polyolefin film comprises between about 10% and about 95%, between about 25% and about 95%, between about 30% and about 95%, between about 40% and about 95%, or between about 50% and about 95%, by weight of the polyolefin film, of recycled polyolefin;
wherein the polyolefin film comprises all of the following:
a) less than 1,000 μg/kg, less than 500 μg/kg, less than 150 μg/kg, or less than 100 μg/kg of isononylphenol, according to the Trace Chemicals Test Method;
b) less than 75 ng/kg, less than 50 ng/kg, or less than 25 ng/kg of PCB 77, according to the Trace Chemicals Test Method;
c) less than 2,000 ng/kg, less than 1,000 ng/kg, less than 200 ng/kg, or less than 100 ng/kg of PCB 118, according to the Trace Chemicals Test Method;
d) less than 45 ng/kg, less than 25 ng/kg, less than 5 ng/kg, or less than 0.85 ng/kg of OCDD, according to the Trace Chemicals Test Method;
e) less than 1.8 ng/kg, less than 1.2 ng/kg, less than 0.8 ng/kg, or less than 0.2 ng/kg of OCDF, according to the Trace Chemicals Test Method;
f) less than 2,500 μg/kg, less than 1,000 μg/kg, less than 500 μg/kg, less than 100 μg/kg, less than 50 μg/kg, or less than 5 μg/kg of bisphenol A, according to the Trace Chemicals Test Method; and
g) less than 1,000 μg/kg, less than 500 μg/kg, less than 100 μg/kg, or less than 50 μg/kg of diisononyl phthalate, according to the Trace Chemicals Test Method; and
wherein the polyolefin film at least partially encloses the consumer product.

87. A package comprising:
a polyolefin film, and
a consumer product;
wherein the polyolefin film comprises a first surface and a second surface;
wherein the polyolefin film comprises between about 10% and about 95%, between about 25% and about 95%, between about 30% and about 95%, between about 40% and about 95%, or between about 50% and about 95%, by weight of the polyolefin film, of recycled polyolefin;
wherein the polyolefin film has an Average Hole Count between about 0.0 and about 10.0, or between about 0.0 and about 8.0, or between about 0.0 and about 5.0, or between about 0.0 and about 3.0, according to the Gel Count Test Method;
wherein the polyolefin film comprises at least one of:
a) less than 1,000 μg/kg, less than 500 μg/kg, less than 150 μg/kg, or less than 100 μg/kg of isononylphenol, according to the Trace Chemicals Test Method;
b) less than 75 ng/kg, less than 50 ng/kg, or less than 25 ng/kg of PCB 77, according to the Trace Chemicals Test Method;
c) less than 2,000 ng/kg, less than 1,000 ng/kg, less than 200 ng/kg, or less than 100 ng/kg of PCB 118, according to the Trace Chemicals Test Method;
d) less than 45 ng/kg, less than 25 ng/kg, less than 5 ng/kg, or less than 0.85 ng/kg of OCDD, according to the Trace Chemicals Test Method;
e) less than 1.8 ng/kg, less than 1.2 ng/kg, less than 0.8 ng/kg, or less than 0.2 ng/kg of OCDF, according to the Trace Chemicals Test Method;
f) less than 2,500 μg/kg, less than 1,000 μg/kg, less than 500 μg/kg, less than 100 μg/kg, less than 50 μg/kg, or less than 5 μg/kg of bisphenol A, according to the Trace Chemicals Test Method; and
g) less than 1,000 μg/kg, less than 500 μg/kg, less than 100 μg/kg, or less than 50 μg/kg of diisononyl phthalate, according to the Trace Chemicals Test Method; and
wherein the polyolefin film at least partially encloses the consumer product.

88. A package comprising:
a polyolefin film, and
a consumer product;
wherein the polyolefin film comprises a first surface forming an outer surface of the polyolefin film and a second surface forming an inner surface of the polyolefin film;
wherein the polyolefin film comprises between about 10% and about 95%, between about 25% and about 95%, between about 30% and about 95%, between about 40% and about 95%, or between about 50% and about 95%, by weight of the polyolefin film, of recycled polyolefin;
wherein the polyolefin film has an Average Hole Count between about 0.0 and about 10.0, or between about 0.0 and about 8.0, or between about 0.0 and about 5.0, or between about 0.0 and about 3.0, according to the Gel Count Test Method;
wherein the polyolefin film has an Inner Surface Spot Count of between about 0.0 and about 100.0, or between about 0.0 and 50.0, or between about 0.0 and about 25.0, or between about 0.0 and about 5.0 and/or an Outer Surface Spot Count of between about 0.0 and about 100.0, or between about 0.0 and 50.0, or between about 0.0 and about 25.0, or between about 0.0 and about 5.0, according to the Gel Count Test Method; and
wherein the polyolefin film at least partially encloses the consumer product.

89. The package of paragraph 88, wherein the polyolefin film comprises at least one of:
a) less than 1,000 µg/kg, less than 500 µg/kg, less than 150 µg/kg, or less than 100 µg/kg of isononylphenol, according to the Trace Chemicals Test Method;
b) less than 75 ng/kg, less than 50 ng/kg, or less than 25 ng/kg of PCB 77, according to the Trace Chemicals Test Method;
c) less than 2,000 ng/kg, less than 1,000 ng/kg, less than 200 ng/kg, or less than 100 ng/kg of PCB 118, according to the Trace Chemicals Test Method;
d) less than 45 ng/kg, less than 25 ng/kg, less than 5 ng/kg, or less than 0.85 ng/kg of OCDD, according to the Trace Chemicals Test Method;
e) less than 1.8 ng/kg, less than 1.2 ng/kg, less than 0.8 ng/kg, or less than 0.2 ng/kg of OCDF, according to the Trace Chemicals Test Method;
f) less than 2,500 µg/kg, less than 1,000 µg/kg, less than 500 µg/kg, less than 100 µg/kg, less than 50 µg/kg, or less than 5 µg/kg of bisphenol A, according to the Trace Chemicals Test Method; and
g) less than 1,000 µg/kg, less than 500 µg/kg, less than 100 µg/kg, or less than 50 µg/kg of diisononyl phthalate, according to the Trace Chemicals Test Method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A package comprising:
a polyolefin film comprising virgin polyolefin and a recycled polyolefin, and
a consumer product;
wherein the polyolefin film comprises a first surface and a second surface;
wherein the polyolefin film comprises from about 10% to about 95%, by weight of the polyolefin film, of the recycled polyolefin;
wherein the recycled polyolefin is from a high-custody sourced feedstock of post-consumer recycled polyolefin material selected to comprise:
(a) from <LOQ to 1000 µg/kg isononylphenol, according to a Trace Chemicals Test Method;
(b) from <LOQ to 75 ng/kg PCB 77, according to the Trace Chemicals Test Method;
(c) from <LOQ to 2000 ng/kg PCB 118, according to the Trace Chemicals Test Method;
(d) from <LOQ to 45 ng/kg OCDD, according to the Trace Chemicals Test Method:
(e) from <LOQ to 1.8 ng/kg OCDF, according to the Trace Chemicals Test Method;
(f) from <LOQ to 2500 µg/kg bisphenol A, according to the Trace Chemicals Test Method; and
(g) from <LOQ to 1000 µg/kg diisononyl phthalate, according to the Trace Chemicals Test Method;
wherein the polyolefin film has an Average Hole Count less than 10.0, according to a Gel Count Test Method;
wherein the polyolefin film has an Average Gel Count less than 25.0, according to the Gel Count Test Method;
wherein the polyolefin film has an Average Relative Gel Height from about 0.0% to about 50.0%, according to the Gel Count Test Method;
wherein the polyolefin film has a Total Spot Count between about 0.0 and about less than 100.0, according to the Gel Count Test Method; and
wherein the polyolefin film at least partially encloses the consumer product.

2. The package of claim 1, wherein the first surface of the polyolefin film comprises printed graphics.

3. The package of claim 1, wherein the second surface of the polyolefin film is devoid of printed graphics.

4. The package of claim 1, wherein the first surface of the polyolefin film forms an inner surface facing toward the consumer product, and wherein the second surface of the polyolefin forms an outer surface facing away from the consumer product.

5. The package of claim 1, wherein the recycled polyolefin consists of the high-custody sourced feedstock of the post-consumer polyolefin material.

6. The package of claim 1, wherein the consumer product comprises at least one of: diapers, wipes, absorbent pants, paper towel, toilet paper, facial tissue, or absorbent underwear.

7. The package of claim 1, wherein the virgin polyolefin is virgin LDPE, and wherein the post-consumer recycled polyolefin material is post-consumer recycled LDPE.

8. The package of claim 1, wherein the high-custody sourced post-consumer polyolefin resin feedstock comprises from 1.0 ng/kg PCB 77 to 75 ng/kg PCB 77 and from 1.0 ng/kg to 2000 ng/kg PCB 118, according to the Trace Chemicals Test Method.

9. The package of claim 1, wherein the high-custody sourced feedstock is a cleaned feedstock from which contaminants that are not polyolefin material have been removed.

10. The package of claim 1, wherein the first surface of the polyolefin film forms an outer surface facing away from the consumer product, and wherein the second surface of the polyolefin film forms an inner surface facing toward the consumer product.

11. The package of claim 10, wherein the polyolefin film has an Inner Surface Spot Count from about 0.0 to about 100.0, according to the Gel Count Test Method.

12. A package comprising:
a polyolefin film comprising a virgin LDPE and a recycled LDPE, and
a consumer product disposed within the polyolefin film;
wherein the polyolefin film comprises a first surface facing away from the consumer product and a second surface facing toward the consumer product;
wherein the polyolefin film comprises from about 10% to about 95%, by weight of the polyolefin film, of the recycled LDPE, wherein the recycled LDPE is from a high-custody sourced feedstock of post-consumer recycled LDPE material selected to comprise:
(a) from <LOQ to 1000 µg/kg isononylphenol, according to a Trace Chemicals Test Method;
(b) from <LOQ to 75 ng/kg PCB 77, according to the Trace Chemicals Test Method;
(c) from <LOQ to 2000 ng/kg PCB 118, according to the Trace Chemicals Test Method:
(d) from <LOQ to 45 ng/kg OCDD, according to the Trace Chemicals Test Method;
(e) from <LOQ to 1.8 ng/kg OCDF, according to the Trace Chemicals Test Method;
(f) from <LOQ to 2500 µg/kg bisphenol A, according to the Trace Chemicals Test Method; and
(g) from <LOQ to 1000 µg/kg diisononyl phthalate, according to the Trace Chemicals Test Method;
wherein the polyolefin film has an Average Hole Count less than 10.0, according to a Gel Count Test Method;
wherein the polyolefin film has an Average Gel Count less than 100.0, according to the Gel Count Test Method; and
wherein the polyolefin film has a Total Spot Count of less than 100.0, according to the Gel Count Test Method.

13. The package of claim 12, wherein the polyolefin film has an Average Gel Height of about 0.00 mm to about 150.00 mm, according to the Gel Count Test Method.

14. The package of claim 12, wherein the polyolefin film has an Average Relative Gel Height from about 0.0% to about 150.0%, according to the Gel Count Test Method.

15. The package of claim 12, wherein the recycled polyolefin consists of the high-custody sourced feedstock of the post-consumer polyolefin LDPE material.

16. The package of claim 12, wherein the high-custody sourced post-consumer polyolefin resin feedstock comprises from 1.0 ng/kg PCB 77 to 75 ng/kg PCB 77 and from 1.0 ng/kg to 2000 ng/kg PCB 118, according to the Trace Chemicals Test Method.

17. The package of claim 12, wherein the high-custody sourced feedstock is a cleaned feedstock from which contaminants that are not polyolefin material have been removed.

18. A package comprising:
a polyolefin film, and
a consumer product;
wherein the polyolefin film comprises a first surface and a second surface, wherein the first surface forms an outer surface facing away from the consumer product, and wherein the second surface forms an inner surface facing toward the consumer product;
wherein the polyolefin film comprises from about 25% and to about 95%, by weight of the polyolefin film, of a recycled polyolefin from a high-custody sourced feedstock of post-consumer recycled polyolefin material selected to comprise:
(a) from <LOQ to 1000 µg/kg isononylphenol, according to a Trace Chemicals Test Method;
(b) from <LOQ to 75 ng/kg PCB 77, according to the Trace Chemicals Test Method:
(c) from <LOQ to 2000 ng/kg PCB 118, according to the Trace Chemicals Test Method:
(d) from <LOQ to 45 ng/kg OCDD, according to the Trace Chemicals Test Method;
(e) from <LOQ to 1.8 ng/kg OCDF, according to the Trace Chemicals Test Method;
(f) from <LOQ to 2500 µg/kg bisphenol A, according to the Trace Chemicals Test Method; and
(g) from <LOQ to 1000 µg/kg diisononyl phthalate, according to the Trace Chemicals Test Method;
wherein the polyolefin film has an Average Hole Count of from about 0.0 to about 10.0, according to a Gel Count Test Method;
wherein the polyolefin film has an Average Gel Count from about 0.0 to about 100.0, according to the Gel Count Test Method;
wherein the polyolefin film has an Average Gel Height from about 0.00 mm to about 150.00 mm, according to the Gel Count Test Method;
wherein the polyolefin film has an Inner Surface Spot Count of from about 0.0 to about 100.0 and/or an Outer Surface Spot Count of from about 0.0 to about 100.0, according to the Gel Count Test Method; and
wherein the polyolefin film at least partially encloses the consumer product.

19. The package of claim 18, wherein the recycled polyolefin consists of the high-custody sourced feedstock of the post-consumer polyolefin resin material.

20. The package of claim 18, wherein the recycled polyolefin comprises at least one of: LLDPE, LDPE, MDPE, HDPE, polypropylene-ethylene interpolymer and copolymers having at least one olefinic constituent, or mixtures thereof.

21. The package of claim 18, wherein the high-custody sourced post-consumer polyolefin resin feedstock comprises from 1.0 ng/kg PCB 77 to 75 ng/kg PCB 77 and from 1.0 ng/kg to 2000 ng/kg PCB 118, according to the Trace Chemicals Test Method.

22. The package of claim 18, wherein the high-custody sourced feedstock is a cleaned feedstock from which contaminants that are not polyolefin material have been removed.

\* \* \* \* \*